United States Patent [19]

Krantz et al.

[11] Patent Number: 5,158,936
[45] Date of Patent: Oct. 27, 1992

[54] ARYLOXY AND ARYLACYLOXY METHYL KETONES AS THIOL PROTEASE INHIBITORS

[75] Inventors: Alexander Krantz, Toronto; Heinz W. Pauls, Mississauga; Roger A. Smith, Milton, all of Canada; Robin W. Spencer, East Lyme, Conn.

[73] Assignee: Syntex (U.S.A.) Inc., Palo Alto, Calif.

[21] Appl. No.: 700,686

[22] Filed: May 15, 1991

Related U.S. Application Data

[60] Division of Ser. No. 127,282, Oct. 8, 1991, Pat. No. 5,055,451, which is a continuation-in-part of Ser. No. 946,737, Dec. 22, 1986, abandoned.

[51] Int. Cl.⁵ .................. A61K 37/02; C07K 5/06; C07K 5/08; C07K 7/06
[52] U.S. Cl. ...................... 514/19; 514/17; 514/18
[58] Field of Search .............. 514/17, 18, 19

[56] References Cited

U.S. PATENT DOCUMENTS

| | | | |
|---|---|---|---|
| 4,539,312 | 9/1985 | Delaney et al. | 514/19 |
| 4,636,492 | 1/1987 | Kettner et al. | 514/19 |
| 4,652,552 | 3/1987 | Kettner et al. | 514/18 |
| 4,692,552 | 9/1987 | Mueller et al. | 562/473 |
| 4,820,691 | 4/1989 | Patel | 514/19 |

FOREIGN PATENT DOCUMENTS 0195212  9/1986  European Pat. Off.

OTHER PUBLICATIONS

CA 65:8822(e) vol. 65, (1966).
CA 97(22): 188158n.
CA 66 (7): 29056w.
T. Toyo-oka et al., *Arzneim.-Forsch/Drug Res.* (1986), vol. 36(I), pp. 190-193, 671-675.
J.-M. Delaissé et al., *Biochem. J.* (1980), vol. 192, pp. 365-368.
J.-M. Delaissé et al., *Biochem. and Biophys. Res. Comm.* (1984), vol. 125, No. 2, pp. 441-447.
E. Kominami et al., *J. Biochem.* (1985), vol. 98, pp. 87-93.
M. T. Bayliss et al., *Biochem. J.* (1978), vol. 171, pp. 149-154.
J. Hollenberg et al., *Proc. Natl. Acad. Sci.* (1981), vol. 78, No. 12, pp. 7742-7744.
M. S. Hudecki et al., *J. Clin. Invest.* (1981), vol. 67, pp. 969-974.
Y. Sanada et al., *J. Biolchem.* (1978), vol. 83, No. 1, pp. 27-33.
R. A. Smith et al., *J. Am. Chem. Soc.* (1988), vol. 110, No. 13, pp. 4429-4431.
A. Krantz et al., *Biochemistry* (1991), vol. 30, No. 19, pp. 4678-4687.
Ahmed, A. K. S. et al., *J. Pharm. Belg.* (1982), vol. 37, No. 3, pp. 214-217.
Muramatsu, N., *Bull. Chem. Soc. Japan* (1966), vol. 39, No. 6, pp. 1273-1279.
Journal of the American Chemical Society (1988), vol. 110, No. 13, pp. 4429-4431.

*Primary Examiner*—Lester L. Lee
*Attorney, Agent, or Firm*—Carol J. Roth; Derek P. Freyberg; Tom M. Moran

[57] ABSTRACT

Thiol protease inhibitors are disclosed having the formula:

$$X-(Y)_m-NH-CH-\underset{\underset{O}{\|}}{C}-CH_2-O-(CO)_n-R' \quad (I)$$
(with R on the CH)

or an optical isomer thereof, or a pharmaceutically acceptable salt thereof, wherein:
n is 0 or 1;
  m is 0, 1 or 2;
  X is H or an N-protecting group;
  each Y is independently an optionally protected α-amino acid residue;
  R is an optionally protected α-amino acid side chain that is H or CH₃ or that is bonded to the α-carbon atom to which it is attached by a methylene, methine or phenyl radial; and
  R' is optionally substituted aryl.

11 Claims, No Drawings

ARYLOXY AND ARYLACYLOXY METHYL KETONES AS THIOL PROTEASE INHIBITORS

This is a division of U.S. patent application Ser. No. 07,127,282, filed Oct. 8, 1991, now U.S. Pat. No. 5,055,451, which is a continuation-in-part of U.S. patent application Ser. No. 06/946,737, filed Dec. 22, 1986, now abandoned, which were assigned to the assignee of the instant invention, and hereby fully incorporated into this disclosure by reference.

BACKGROUND OF THE INVENTION

Field of Invention

This invention relates generally to inhibitors of thiol (cysteine) proteases, and most particularly to inhibitors of Cathepsin B (Cat-B).

Proteases are a significant class of enzymes, important in normal physiology but also associated with a number of disease states, including but not limited to inflammation, metastasis, tissue damage following myocardial infarction, bone resorption, and muscle wasting in dystrophic diseases.

Cathepsin B is a cysteine protease involved in normal protein degradation, and as such is generally located in the lysosomes of cells. It is essentially ubiquitous in its tissue distribution. In extracellular or cell-surface forms, Cathepsin B or Cathepsin B-like enzymes have a suggested involvement in several of the above states.

In recent years, investigators have reported a number of synthetic protease inhibitors: Rasnick, in U.S. Pat. No. 4,518,528 (issued May 21, 1985), and in *Anal. Biochem.* 149, 461–465 (1985), discloses α-amino fluoromethyl ketones as irreversible inhibitors of serine or cysteine protease; Shaw, et al., in *Biochemistry* 16, 5857 (1977), *Biochem. Biophys. Res. Commun.* 89, 1354 (1979), and *J. Biol. Chem.* 256, 1923 (1981), disclose peptidyl diazomethylketones as irreversible inhibitors of thiol proteases; and Hanada, et al., *Agric. Biol. Chem.* 42, 529 (1978) and *Biochem. J.* 201, 189 (1982) disclose epoxysuccinyl peptides as inhibitors of thiol proteases. A limited number of peptidyl acetyloxy-methyl ketones have been reported as enzyme inhibitors: McMurray and Dyckes, in *Biochemistry* 25, 2298 (1986) disclose an acetyloxymethyl ketone as a reversible inhibitor of the serine protease trypsin, and Larsen and Shaw, in *J. Med. Chem.* 19, 1284 (1976) disclose acetyloxymethyl ketones as reversible inhibitors of the serine protease chymotrypsin.

A survey of this prior art shows that there is a need for potent and specific thiol protease inhibitors. In particular, there is a need for chemically stable inhibitors that minimize the likelihood of non-specific reactions with plasma or cellular constituents.

SUMMARY OF THE INVENTION

This invention is directed to compounds of the formula:

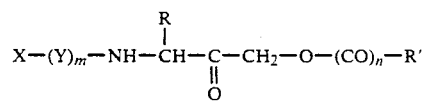

or an optical isomer thereof, or a pharmaceutically acceptable salt thereof, wherein:
n is 0 or 1;
m is 0, 1 or 2;
X is H or an N-protecting group;
each Y is independently an optionally protected α-amino acid residue;
R is an optionally protected α-amino acid side chain that is H or $CH_3$ or that is bonded to the α-carbon atom to which it is attached by a methylene, methine or phenyl radical; and
R' is optionally substituted aryl.

Another aspect of the invention is a method for inhibiting thiol proteases by administering a therapeutically effective amount of a compound of Formula I to a mammal in need thereof, such as a human.

Yet another aspect of the invention is a method for treating or preventing tissue damage in myocardial infarction by administering a therapeutically effective amount of a compound of Formula I to a mammal in need thereof, such as a human.

Still another aspect of the invention is a method of treating inflammation by administering a therapeutically effective amount of a compound of Formula I to a mammal in need thereof, such as a human.

A further aspect of the invention is a method of treating or preventing bone resorption by administering a therapeutically effective amount of a compound of Formula I to a mammal in need thereof, such as a human.

Another aspect of the invention is a method of slowing or preventing tissue damage in dystrophic disease by administering a therapeutically effective amount of a compound of Formula I to a mammal in need thereof, such as a human.

Still another aspect of the invention is a method promoting weight gain by administering an effective amount of a compound of Formula I to a plant or animal, such as poultry, cattle, or pigs.

DETAILED DESCRIPTION

Definitions

For the purposes of this invention, the following terms are to be understood to have the meanings set forth below.

"Alkyl" means a branched or unbranched, saturated aliphatic hydrocarbon radical, having the number of carbon atoms specified, or if no number is specified, having up to 8 carbon atoms. The prefix "alk-" is also indicative of a radical having up to 8 carbon atoms in the alkyl portion of that radical, unless otherwise specified. Examples of alkyl radicals include methyl, ethyl, n-propyl, isopropyl, n-butyl, tert-butyl, n-pentyl, n-hexyl, and the like. The terms "lower alkyl" and "alkyl of 1 to 4 carbon atoms" are synonymous and used interchangeably.

Abbreviations are used herein as follows:
"Ac" means acetyl.
"Boc" means t-butyloxycarbonyl.
"CBZ" means benzyloxycarbonyl.
"DCC" means N,N'-dicyclohexylcarbodiimide.
"EDCI" means N-ethyl-N'-(3-dimethylaminopropyl)-carbodiimide.
"NMM" means N-methylmorpholine.
"Tosyl" means 4-toluenesulfonyl.

"α-Amino acids" as used herein include naturally occurring and commercially available amino acids and optical isomers thereof. Typical natural and commercially available amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, o-, m-, and p-tyrosine, tryptophan, glutamine, asparagine, proline and hydroxyproline. An amino acid residue is an amino acid radical —NHCH(R)C(O)—, wherein R is an amino acid side chain, except for the amino acid residues of proline and hydroxyproline which are —N(CH$_2$CH$_2$CH$_2$)CHC(O)— and —N(CH$_2$CHOHCH$_2$)CHC(O)—, respectively. An amino acid side chain is a radical found on the α-carbon of an α-amino acid as defined herein, where the radical is either hydrogen (side chain of glycine), methyl (side chain of alanine), or is a radical bonded to the α-carbon by a methylene (—CH$_2$—),

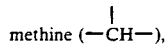

methine (—CH—), or phenyl group. A hydrophobic amino acid residue or side chain is one in which the side chain is uncharged at physiological pH.

"Halo" means bromo, chloro or fluoro.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Optionally substituted aryl" means optionally substituted phenyl or 1-naphthyl; or unsubstituted 2-naphthyl or 9-anthracyl.

"Optionally substituted phenyl" means unsubstituted phenyl; and phenyl having 1 to 5 fluoro substituents; and phenyl having 1 to 3 substituents, where the substituents are independently selected from the group consisting of lower alkyl, lower alkoxy, nitro, halo, acetyl, benzoyl, hydroxy, amino, methylamino, dimethylamino, diethylamino, methylthio, cyano, trifluoromethyl, phenylsulfonamidocarbonyl(—CONHSO$_2$C$_6$H$_5$), —COOH, —CONH$_2$, —COOR$^2$, NHCOR$^2$ wherein R$^2$ is lower alkyl; and 2,3,5,6-tetramethyl-4-carboxy-phenyl(—C$_6$(CH$_3$)$_4$—COOH). "Optionally substituted 1-naphthyl" includes unsubstituted 1-naphthyl; and 1-naphthyl substituted at the 2-position with lower alkyl, lower alkoxy, or trifluoromethyl.

"Optionally protected α-amino acid residue" means an α-amino acid residue having an optionally protected α-amino acid side chain.

"Optionally protected α-amino acid side chain" includes an unprotected α-amino acid side chain such as the H in glycine, the CH$_3$ in alanine, and the CH$_2$OH in serine; or if the side chain includes heteroatoms such as oxygen, sulfur, or nitrogen, the heteroatoms on the side chain can optionally be protected with an O-, S-, or N-protecting group.

An "O-, S-, or N-protecting group" is a radical attached to an oxygen, sulfur, or nitrogen atom, respectively, which radical serves to protect the oxygen, sulfur, or nitrogen functionality against undesired reactions and/or to modify the properties of the molecule to which it is attached (e.g., solubility, lipophilicity, bioavailability, etc.). Such protecting groups are well known in the art, and many are described in "The Peptides," E. Gross and J. Meienhofer, Eds., Vol. 3, Academic Press, NY (1981), and "Chemistry of the Amino Acids," J. P. Greenstein and M. Winitz, Vol. 2, J. Wiley and Sons, NY (1961).

"N-Protecting groups" for amino functionalities of amino acids, at the peptide N-terminal, or on amino acid side chains are well known in the art. An exemplification of known amino N-protecting groups is included in "The Peptides," E. Gross and J. Meienhofer, Eds., Academic Press, NY (1981), Vol. 3, Chapter 1; "Protective Groups in Organic Synthesis," T. W. Greene, J. Wiley and Sons, NY (1981), Chapter 7; and "Chemistry of the Amino Acids," J. P. Greenstein and M. Winitz, J. Wiley and Sons, NY (1961), Vol. 2, pp. 885–924; other (less well-known) N-protecting groups include the methoxysuccinyl group (CH$_3$OCOCH$_2$CH$_2$CO—), the hydroxysuccinyl group (HOOCCH$_2$CH$_2$CO—), the p-methoxycarbonyl-benzoyl group (p—CH$_3$OCO—C$_6$H$_4$CO—), the p-phenylsulfonamidocarbonyl-benzoyl group (p—C$_6$H$_5$SO$_2$NHCO—C$_6$H$_4$CO—), and the 2-(1-adamantyl)-ethoxycarbonyl group.

Generally, these N-protecting groups can be considered to fall within five classes: N-acyl, N-alkoxycarbonyl, N-arylmethoxycarbonyl, N-arylmethyl, and N-arylsulfonyl protecting groups. An N-acyl protecting group is a lower alkyl carbonyl radical, a trifluoroacetyl radical, a methoxysuccinyl radical (CH$_3$OCOCH$_2$CH$_2$CO—), a hydroxysuccinyl radical (HOOCCH$_2$CH$_2$CO—) or a phenylcarbonyl (benzoyl) radical optionally substituted on the phenyl ring with p-methoxycarbonyl, p-phenylsulfonamidocarbonyl(p—C$_6$H$_5$SO$_2$NHCO—), p-methoxy, or p-nitro. An N-alkoxycarbonyl protecting group is a lower alkoxycarbonyl radical or a 2-(1-adamantyl)ethoxycarbonyl radical. An N-arylmethoxycarbonyl protecting group is a 9-fluorenemethoxycarbonyl radical (Fmoc); or benzyloxycarbonyl radical which can optionally be substituted on the aromatic ring with p-methoxy, p-nitro, p-chloro, or o-(N,N-dimethyl-carboxamido). An N-arylmethyl protecting group is a benzyl radical, which can optionally be substituted on the aromatic ring with p-methoxy, p-nitro, or p-chloro. An N-arylsulfonyl protecting group is a phenylsulfonyl radical, which can optionally be substituted on the aromatic ring with p-methyl ("tosyl") or p-methoxy.

"N-protecting groups" for guanidino functionalities on arginine amino acid side chains are known in the art, and described in "The Peptides," Vol. 3, pp. 60–70 and "Chemistry of the Amino Acids," Vol. 2, pp. 1068–1077, as cited earlier. These include the nitro, p-toluenesulfonyl, p-methoxyphenylsulfonyl, CBZ, and Boc N-protecting groups.

"N-protecting groups" for imidazole functionalities on histidine amino acid side chains are known in the art, and described in "The Peptides," Vol. 3, pp. 70–80, and "Chemistry of the Amino Acids," Vol. 2, pp. 1060–1068, as cited earlier. These include the benzyl, triphenylmethyl (trityl), 2,4-dinitrophenyl, p-toluenesulfonyl, benzoyl, and CBZ N-protecting groups.

"N-protecting groups" for indole functionalities on tryptophan amino acid side chains are known in the art and described in "The Peptides," Vol. 3, pp. 82–84, as cited earlier. These include the formyl and CBZ N-protecting groups.

"O-protecting groups" for hydroxy functionalities on amino acid side chains are known in the art and described in "The Peptides," Vol. 3, pp. 169–201, and "Chemistry of the Amino Acids," Vol. 2, pp.

1050–1056, as cited earlier. For aliphatic hydroxy functionalities, suitable O-protecting groups include benzyl, tert-butyl, and methyl groups. For aromatic hydroxy functionalities, suitable O-protecting groups include the benzyl, tert-butyl, methyl, CBZ, and tosyl groups.

"O-protecting groups" for carboxy functionalities on amino acid side chains are well known in the art and described in "The Peptides," Vol. 3, pp. 101–135, as cited earlier, and include the methyl, ethyl, tert-butyl, and benzyl groups.

"S-protecting groups" for thiol functionalities on amino acid side chains are known in the art, and described in "The Peptides," Vol. 3, pp. 137–167, and "Chemistry of the Amino Acids," pp. 1077–1092, as cited earlier. These include the methyl, tert-butyl, benzyl, p-methoxyphenylmethyl, ethylamino-carbonyl, and CBZ groups.

"Pharmaceutically acceptable salts" include both acid and base addition salts.

"Pharmaceutically acceptable acid addition salt" refers to those salts which retain the biological effectiveness and properties of the free bases and which are not biologically or otherwise undersirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

The compounds of the present invention may be single stereoisomers, racemates, or mixtures of diastereomers. Unless otherwise specified, the asymmetric carbon atoms in the compounds described herein are all in the (S)-configuration, as in natural L-amino acids. However, the scope of the subject invention herein is not to be considered limited to the (S) optical isomers, but to encompass all optical isomers of the compounds and mixtures thereof.

The nomenclature used herein is such that the claimed compounds and intermediates are named as ketones derived from the analogous carboxylic acid, more specifically as substituted-methyl ketones derived from the analogous carboxylic acid. For example, intermediate (3) where X is benzoyl, m is 0, R is methyl, and Z is Br would be named "N-benzoyl-L-alanine bromomethyl ketone," as it is derived from the analogous carboxylic acid (2) (where X is benzoyl, m is 0, and R is methyl) named "N-benzoyl-L-alanine." Similarly, the compound of Formula I where X is CBZ, m is 1, Y is L-phenylalanyl, R is methyl, n is 0 and R' is pentafluorophenyl, is named "N-benzyloxycarbonyl-L-phenylalanyl-L-alanine pentafluorophenoxymethyl ketone", and the compound of Formula I where X is CBZ, m is 1, Y is L-phenylalanyl, R is methyl, n is 1, and R' is 2,6-bis(trifluoromethyl)phenyl, is named "N-benzyloxycarbonyl-L-phenylalanyl-L-alanine 2,6-bis(trifluoromethyl)benzoyloxymethyl ketone". These two compounds are derived from the carboxylic acid "N-benzyloxycarbonyl-L-phenylalanyl-L-alanine."

PREFERRED EMBODIMENTS

Within the broadest scope of the invention, there are several preferred embodiments.

It is generally preferred that m be 1 or 2. When m is 1, Y (the amino acid) is preferably a natural amino acid and more preferably a hydrophobic amino acid residue such as L-phenylalanyl, L-leucyl, and L-alanyl. It is more preferred, when m is 1, that Y is L-phenylalanyl or L-leucyl. When m is 2, the two Y amino acids are preferably independently chosen from the hydrophobic amino acid residues. Especially preferred amino acid sequences when m is 2 are glycyl-L-phenylalanyl, L-leucyl-L-leucyl, L-phenylalanyl-L-phenylalanyl, and L-alanyl-L-phenylalanyl. It is most preferred that m is 1 and Y is L-phenylalanyl.

The preferred optionally protected α-amino acid side chains (R) are:

hydrogen;

lower alkyl;

—$(CH_2)_a WR^3$ wherein a is 1 or 2, and W is oxygen or sulfur, and $R^3$ is methyl or benzyl;

—$CH(CH_3)OCH_2Ph$;

—$(CH_2)_b NHR^4$ wherein b is 3 or 4, and $R^4$ is H, Ac, Boc, or CBZ;

—$(CH_2)_c C(O)R^5$ wherein c is 1 or 2, and $R^5$ is amino, methoxy, or benzyloxy; and —$(CH_2)_d R^6$ wherein d is 0, 1, or 2 and $R^6$ is phenyl, or wherein d is 1 and $R^6$ is phenyl monosubstituted with methoxy or benzyloxy.

The more preferred R radicals are the side chains of: glycine (i.e., hydrogen); alanine (i.e., methyl); methionine (i.e., 2-(methylthio)-ethyl); phenylalanine (i.e., benzyl); O-benzylserine (i.e., benzyloxymethyl); S-benzylcysteine (i.e., benzylthiomethyl); O-benzylthreonine (i.e., 1-(benzyloxy)-ethyl); and lysine (i.e., 4-aminobutyl).

It is most preferred that R is hydrogen, methyl, benzyloxymethyl or 4-aminobutyl.

It is preferred that X in Formula I be hydrogen, or an amino N-protecting group chosen from the list: trifluoroacetyl, acetyl, methoxysuccinyl, hydroxysuccinyl, benzoyl, p-methoxycarbonyl-benzoyl(p—$CH_3OCO$—$C_6H_4CO$—), p-phenylsulfonamidocarbonylbenzoyl (p—$C_6H_5SO_2NHCO$—$C_6H_4CO$—), Boc, isobutyloxycarbonyl, methoxycarbonyl, CBZ, phenylsulfonyl, and tosyl. It is more preferred that X be hydrogen, acetyl, methoxysuccinyl, hydroxysuccinyl, benzoyl, p-methoxycarbonyl-benzoyl(p—$CH_3OCO$—$C_6H_4CO$—), p-phenylsulfonamidocarbonyl-benzoyl (p—$C_6H_5SO_2NHCO$—$C_6H_4CO$—), Boc, CBZ, or tosyl. It is most preferred that X be CBZ, methoxysuccinyl, hydroxysuccinyl, p-methoxycarbonyl-benzoyl (p—$CH_3OCO$—$C_6H_4CO$—), or p-phenylsulfonamidocarbonyl-benzoyl (p—C$_6$H$_5$SO$_2$NH-CO—C$_6$H$_4$CO—).

When n is 1, it is preferred that R' is selected from:
phenyl;
phenyl substituted in the 4-position with 4cetylamino, acetyl, benzoyl, halo, amino, methylamino, dimethylamino, diethylamino, hydroxy, methoxy, ethoxy, methylthio, cyano, nitro, phenylsulfonamidocarbonyl, trifluoromethyl, methyl, ethyl, propyl, isopropyl, butyl, or tert-butyl;
phenyl disubstituted in the 3,5-positions with hydroxy or trifluoromethyl;
phenyl disubstituted in the 2,6-positions with methyl, trifluoromethyl, methoxy, fluoro, or chloro;
pentafluorophenyl;
2,4,6-trimethyl- or 2,4,6-triisopropylphenyl;
2,6-dimethyl-4-methoxycarbonyl-phenyl;
2,6-dimethyl-4-phenylsulfonamidocarbonyl-phenyl;
2,3,5,6-tetramethyl-4-carboxy-phenyl (—C$_6$(CH$_3$)$_4$—COOH);
1-naphthyl optionally substituted in the 2-position with methyl, methoxy, or ethoxy;
2-naphthyl; and
9-anthracyl.

When n is 1, it is more preferred that R' is selected from:
2,6-dimethyl-4-methoxycarbonyl-phenyl;
2,6-dimethyl-4-phenylsulfonamidocarbonyl-phenyl;
2,6-bis(trifluoromethyl)-phenyl;
2,4,6-trimethylphenyl;
2,3,5,6-tetramethyl-4-carboxy-phenyl;
2-methyl-1-naphthyl; and
9-anthracyl.

When n is 1, it is most preferred that R' is 2,6-bis(trifluoromethyl)phenyl, 2,4,6-trimethylphenyl, or 2,3,5,6-tetramethyl-4-carboxy-phenyl.

In Formula I, when n is 0, it is preferred that R' is selected from:
phenyl;
phenyl substituted with 1 or 2 fluorine atoms;
2,3,5,6- or 2,3,4,6-tetrafluorophenyl;
pentafluorophenyl;
phenyl disubstituted in the 2,6-positions with methyl, methoxy, chloro, isopropyl, or phenyl;
3,5-bis(trifluoromethyl)phenyl; and
phenyl monosubstituted in the 2 or 4 position
with cyano, methoxy, hydroxy, acetoxy, nitro, acetamido, or C(O)Q (wherein Q is amino, H or lower alkoxy).

When n is 0 it is more preferred that R' is selected from:
2,3,5,6- or 2,3,4,6-tetrafluorophenyl; pentafluorophenyl; and
phenyl monosubstituted in the 2-position with nitro, acetamido or CONH$_2$.

When n is 0 it is most preferred that R' is pentafluorophenyl.

For the invention as a whole, the presently specifically preferred compounds are:
N-Benzyloxycarbonyl-L-phenylalanyl-L-alanine pentafluorophenoxymethyl ketone;
N-Benzyloxycarbonyl-L-phenylalanyl-O-benzyl-L-threonine pentafluorophenoxymethyl ketone;
N-Benzyloxycarbonyl-L-phenylalanyl-L-alanine 2-carbamoyl-phenoxymethyl ketone;
N-Benzyloxycarbonyl-L-phenylalanyl-L-alanine 4-nitrophenoxymethyl ketone;
N-Benzyloxycarbonyl-L-phenylalanyl-L-alanine 2,6-bis(trifluoromethyl)benzoyloxymethyl ketone;
N-Benzyloxycarbonyl-L-phenylalanyl-L-alanine 2,4,6-trimethylbenzoyloxymethyl ketone;
N-Benzyloxycarbonyl-L-phenylalanyl-O-benzyl-L-serine 2,4,6-trimethylbenzoyloxymethyl ketone;
N-Benzyloxycarbonyl-L-phenylalanyl-S-benzyl-L-cysteine 2,6-bis(trifluoromethyl)benzoyloxymethyl ketone;
N-Benzyloxycarbonyl-L-phenylalanyl-O-benzyl-L-threonine 2,4,6-trimethylbenzoyloxymethyl ketone;
N-Benzyloxycarbonyl-L-phenylalanyl-L-alanine 2-methyl-1-naphthoyloxymethyl ketone;
N-Benzyloxycarbonyl-L-phenylalanyl-glycine 2,4,6-trimethylbenzoyloxymethyl ketone;
N-Methoxysuccinyl-L-phenylalanyl-L-alanine 2,4,6-trimethylbenzoyloxymethyl ketone;
N-Hydroxysuccinyl-L-phenylalanyl-L-alanine 2,4,6-trimethylbenzoyloxymethyl ketone;
N-(4-Phenylsulfonamidocarbonyl-benzoyl)-L-phenylalanyl-L-alanine 2,4,6-trimethylbenzoyloxymethyl ketone; N-Benzyloxycarbonyl-L-phenylalanyl-L-lysine 2,4,6-trimethylbenzoyloxymethyl ketone, hydrochloride salt; and
N-Benzyloxycarbonyl-L-phenylalanyl-L-alanine 2,3,5,6-tetramethyl-4-carboxy-benzoyloxymethyl ketone.

While the broadest scope of the invention includes individual R and S stereoisomers as well as a mixture of stereoisomers, the preferred chirality at all asymmetric carbon atoms is S (i.e., L) as in natural amino acids.

UTILITY AND ADMINISTRATION

Cathepsin B inhibitors have several pharmaceutical applications, discussed below, based on therapeutic effects of inhibition of the enzyme expressed in disease states.

Tissue Damage in Myocardial Infarction

Recent studies have shown that peptidyl epoxide inhibitors of Cathepsin B are effective in reducing tissue damage in infarcted myocardial tissue (Tsuchida, et al, *Biol. Chem. Hoppe-Seyler* 367:39 (1986); Toyo-oka, et al., *Arzneim-Forsch./Drug Res.* 36(I): 190–193 (1986); Toyo-oka, et al., *Arzneim-Forsch./Drug Res.* 36(I): 671–675 (1986)). The inhibitor was effective when given before and up to 3 hours after coronary ligation of rabbits.

Inhibition of Bone Resorption

Both Cathepsin B and collagenase are involved in bone resorption. Delaisse, et al., (*Biochem. Biophys. Res. Commun.* 125: 441–447 (1984), and *Biochem. J.* 192: 365–368 (1980)) show that secretion of Cathepsin B correlates with hormone-induced calcium loss, hydroxyproline loss, and bone resorption in cultured embryonic mouse calvaria, and that this resorption is inhibited by a Cathepsin B inhibitor. When given in vivo to rats, Cathepsin B inhibitors result in a fall in serum calcium and hydroxyproline levels.

Metastasis

Cathepsin B has been associated with malignant tumors and is implicated in the process of metastasis. The enzyme has been characterized from many different tumor types. Some recent studies by several laboratories have examined the particular source of this activity. Sloane and associates have demonstrated that the Cathepsin B-like activity is from viable tumor cells, not from host macrophages or necrotic tumor cells in their rodent tumor studies (Ryan, et al., *Cancer Res.* 45: 3636 (1985) and Sloane & Honn, *Cancer Metastasis Rev.* 3: 249 (1984))), and also that a Cathepsin B-like enzyme appears to be associated with the plasma membrane of some neoplastic cells (Pietras, et al., *J. Biol. Chem.* 256:8536 (1984) and Sloane & Honn, *Cancer Metastasis Rev.* 3:249 (1984)).

In other tumor systems the Cathepsin B-like enzyme appears to be associated with the host leukocytes, especially macrophages. Its release and possibly its increased quantity is stimulated by tumor cells (Baici, et al., in: *Tumour Progression and Markers*, pp. 47–50, (1982)).

Since degradation of collagen is a key step in metastasis (Liotta, et al., *Ann. Rev. Biochem.* 55: 1037–1057 (1986)), it is noteworthy that Cathepsin B is capable of activating latent collagenase (Baici, et al., in: *Tumour Progression and Markers*, pp. 47–50, (1982)), as well as cleaving collagen itself in the non-helical regions.

Inflammation

The evidence that Cathepsin B and other thiol proteases play a role in inflammation is circumstantial but compelling. Kominami, et al. (*J. Biochem.* 98:87 (1985)) have shown that the concentration of Cathepsin B is 30- to 40-fold higher in rat macrophages than in lymphocytes or neutrophils. The enzyme level is elevated more than 6-fold in inflammatory macrophages.

Calpains (i.e., calcium-activated neutral proteases) are thiol proteases with an active site homology to Cathepsin B (Sakihama, et al, *Proc. Natl. Acad. Sci.- (USA)* 82: 6075–6079 (1985); Ohno, et al, Nature 312: 566–570 (1984)). Pontremoli & Melloni (*Ann. Rev. Biochem.* 55: 455–481 (1986)) suggest that calpains play an important role in the activation of neutrophils and platelets.

The role of Cathepsin B in other inflammatory processes is suggested by its elevated levels in osteoarthritic cartilage (Bayliss & Ali, *Biochem. J.*, 171: 149 (1978)) and gingivitis fluid (Eisenhauer, et al., *J. Dent. Res.* 62: 917 (1983)).

Muscular Dystrophy

Muscle wasting in Duchenne muscular dystrophy is principally due to accelerated protein catabolism (Kar, *Biochemical Medicine* 27: 361–366 (1982)) with both serine protease(s) and Cathepsin B implicated (Sanada, et al, *J. Biochem.* 83: 27–33). Hudecki, et al. (*J. Clin. Invest.* 67: 969–974 (1981)) have shown that intraperitoneal (i.p.) leupeptin (a natural Cathepsin B inhibitor) significantly reduces plasma creatine phosphokinase (a marker for tissue damage) and may also improve righting ability in dystrophic chickens. Sher, et al. (*Proc. Natl. Acad. Sci.* (USA) 78: 7742–7744 (1981)) have similarly shown that i.p. leupeptin prevents or delays the onset of muscular dystrophy in a genetic (mouse) model.

Weight Gain Promotion in Agriculture

Inhibition of normal lysosomal Cathepsin B might slow protein turnover and thereby serve as a weight gain promoter. Recent patents (U.S. Pat. No. 4,510,130 and EP 144,993; Platt & Stracher, Genetic Diagnostics Corp. (*Chem. Abstract.* 103: 5442a and 70330h) are based on increased growth observed when leupeptin was given to hamsters, chickens, mice, and peas.

Administration

Administration of the active compounds and salts described herein can be via any of the accepted modes of administration for agents which have the intended therapeutic use. These methods include oral, parenteral, topical and otherwise systemic or aerosol forms.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For systemic administration via suppository, traditional binders and carriers include, e.g. polyalkalene glycols or triglycerides. Such suppositories may be formed from mixtures containing active ingredient in the range of 0.5%–10%; preferably 1–2%.

The amount of active compound administered will of course, be dependent on the subject being treated, the severity of the affliction, the manner of administration and the judgment of the prescribing physician. However, an effective dosage for a human is in the range of about 0.01 to about 25 mg/kg/day, preferably about 0.1 to about 10 mg/kg/day, and most preferably about 0.75 to about 3 mg/kg/day.

METHODS OF PREPARATION

The compounds of Formula I are prepared by performing a sequence of reactions as shown in Reaction Schemes I, II and III. In general, the first step of this procedure involves the preparation of an N-protected amino acid or peptide (2) having an unprotected C-terminal carboxy group, but with protected amino acid side chain functionalities. Methods for the synthesis of such peptidyl derivatives are well established in the art. The N-protected amino acid or peptide (2), which in some cases is also commercially available, is then converted, by way of hydrochlorination or hydrobromination of a diazomethyl ketone intermediate, to the analogous N-protected amino acid or peptidyl chloromethyl or bromomethyl ketone (3). A displacement reaction of the chloromethyl or bromomethyl ketone (3) by an aromatic alcohol or carboxylic acid then provides the compounds of the invention wherein X is an N-protecting group. Application of standard peptidyl deprotection procedures affords additional compounds of the invention, for example, those compounds of Formula I wherein X is hydrogen. Individual steps of the overall synthetic procedure are described in detail below.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the Examples. However, other equivalent separation or isolation procedures could, of course, also be used.

The salt products are also isolated by conventional means. For example, the reaction mixtures may be evaporated to dryness, and the salts can be further purified by conventional methods.

The compounds of Formula I in free base form may be converted to the acid addition salts by treating with a stoichiometric excess of the appropriate organic or inorganic acid, such as, for example, acetic, oxalic, maleic, phosphoric, pyruvic, hydrochloric or sulfuric acid and the like. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of Formula I may be decomposed to the corresponding free base by treating with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent being used as the medium for the procedure.

The salt derivatives of the compounds of Formula I are prepared by treating the corresponding free acids of the compounds of Formula I with at least one molar equivalent of a pharmaceutically acceptable base. Representative pharmaceutically acceptable bases are sodium hydroxide, potassium hydroxide, ammonium hydroxide, calcium hydroxide, trimethylamine, lysine, caffeine, and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, or dioxane. The molar ratio of compounds of Formula I to base used are chosen to provide the ratio desired for any particular salt.

The compounds of the present invention may be prepared from L-amino acids, D-amino acids, or racemic mixtures thereof. Single enantiomers (stereoisomers) of Formula I are prepared by using L-amino acids and/or D-amino acids as starting materials. When m is 0, racemates of Formula I are obtained by using racemic mixtures of amino acids. When m is 1 or 2, mixtures of diastereomers of Formula I are obtained by using racemic mixtures of amino acids. Using a combination of racemic amino acids and L- and/or D-amino acids also yields mixtures of diastereomers of Formula I. If desired, mixtures of diastereomers of Formula I may be separated into pure stereoisomers by conventional means, for example by fractional crystallization or chromatography. Generally, L-amino acids are used, thereby providing single enantiomers of Formula I in which all asymmetric carbon atoms have the (S)-configuration.

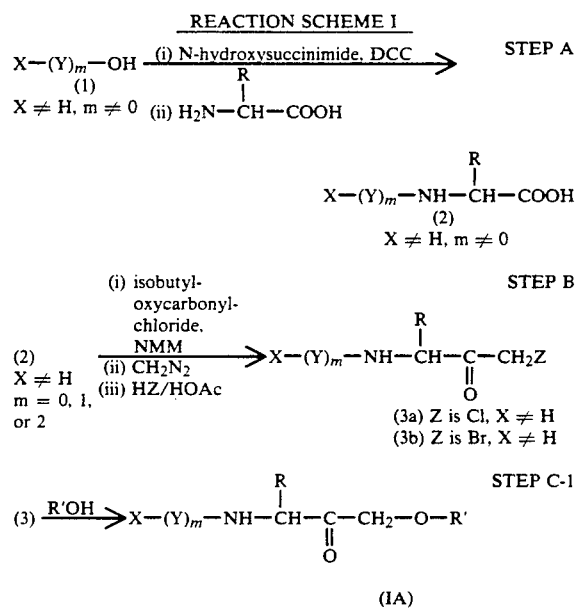

Step A

Turning now to Reaction Scheme I, N-protected starting materials (1) wherein m is 1 are generally commercially available, or can be made by standard methods of N-protection and, if necessary, protection of any amino acid side chain heteroatom functionalities. These methods are known to one of ordinary skill in the art, and have been described above and in "The Peptides," Vol. 3; "Chemistry of the Amino Acids," Vol. 2; and "Protective Groups in Organic Synthesis" as cited above. When m is 2, N-protected starting materials (1) are in some cases commercially available, or can otherwise be prepared by standard synthetic peptide methodology (described below), an example of which is described herein as Step A. Starting materials (i) and (ii) are commercially available, except for certain examples of amino acids (ii) with unprotected heteroatoms on the side chain. These exceptions of (ii) can be readily prepared by one of ordinary skill in the art by methods relating to the protection of amino acid side chains, disclosed in "The Peptides," Vol. 3; and "Chemistry of the Amino Acids," Vol. 2, as cited above.

Intermediates (2), when not commercially available, were readily prepared by standard synthetic peptide methodology commonly known to those skilled in the art (for example as described in "The Practice of Peptide Synthesis," M. Bodanszky, Springer-Verlag, NY (1984); and "The Peptides," E. Gross, J. Meienhofer, Eds., Vols. 1 and 3, Academic Press, NY (1979)). Practical synthetic routes from (1) to (2) include (a) the formation of an active ester followed by coupling with an amino acid; and (b) the coupling of an N-protected amino acid with an amino acid ester (via the mixed carbonic anhydride, or by the use of an N,N'-dialkyl-carbodiimide), followed by alkaline hydrolysis of the C-terminal ester group. Suitable active esters for use in method (a) include N-hydroxysuccinimide esters, 4-nitrophenyl esters, pentafluorophenyl esters, 1-hydroxybenzotriazole esters, and the like. An example of method (a), involving the formation of an N-hydroxysuccinimide active ester followed by reaction with an amino acid, is shown in Step A of Scheme I. In a similar manner, as is well known in the art, intermediates (2) containing two amino acid residues (m=1) may be reacted again as in Step A to provide intermediates (2) containing three amino acid residues (m=2). Alternatively, intermediates (2) containing three amino acid residues (m=2) are prepared by reacting an N-protected amino acid active ester with a commercially available dipeptide. As will be clear to one skilled in the art, the preferred method of preparation of any particular intermediate (2) will depend on considerations regarding to commercial availability of starting materials, coupling methods, protection methods, and deprotection methods.

Step A is directed to the formation of an active ester followed by coupling with an amino acid. According to this method, an N-protected amino acid or peptide is treated with an appropriate activating alcohol, preferably N-hydroxysuccinimide (or alternatively, for example, 1-hydroxybenzotriazole), followed by addition of a dialkylcarbodiimide, preferably DCC (or alternatively N-ethyl-N-dimethylaminopropyl-carbodiimide), to yield the activated ester. This reaction is most preferably carried out at 0° C. for about 2 hours, followed by reaction overnight at room temperature, but can suitably be carried out at any temperature between about −20° to 100° C., preferably −10° to 40° C., for a total period of time in the range of from about 2 hours to about 2 days, preferably 4 to 24 hours. Suitable solvents for the reaction include polar aprotic solvents, such as, dimethylformamide (DMF), dioxane, dimethoxyethane (DME), ethyl acetate, or tetrahydrofuran (THF). Preferred solvents are THF or dioxane, with THF as the most preferred.

The active ester intermediate (not shown) can be isolated by any standard means, such as by filtration of the reaction mixture followed by evaporation of the filtrate. The residue (activated ester) can then optionally be purified by extractive workup.

The active ester, which in some cases is also commercially available, is reacted with a mixture of amino acid (ii) and a tertiary amine, in an aqueous polar solvent such as aqueous dioxane, aqueous THF, aqueous DMF, preferably in aqueous dioxane or THF (and most preferably 1:1 dioxane/water). Exemplary tertiary amines include but are not limited to triethylamine, N-methylmorpholine, triethylenediamine, with triethylamine being preferred. Suitable temperature ranges for this reaction are −20° to 80° C., but preferably the temperature is in the range of −10° to 50° C., and most preferably room temperature. The reaction is generally left overnight but can suitably be allowed to proceed for a period of time in the range of 10 minutes to over 2 days, more preferably about 2 hours to about 24 hours.

The N-protected peptide of formula (2) is then isolated by conventional means, for example by acidification followed by extractive workup. A detailed example of Step A is provided in Preparation 1. Procedures which make use of commerically available active esters are given in Preparations 2(a) and 2(b). An example of the synthesis of (2) by the coupling of an N-protected amino acid with an amino acid ester (by the use of an N,N'-dialkyl-carbodiimide), followed by alkaline hydrolysis of the C-terminal ester group (reaction scheme not shown) is given in Preparation 3.

Step B

Continuing with Reaction Scheme I, in Step B the N-protected amino acid or peptide (2) is converted to the corresponding chloromethyl ketone (3a) by hydrochlorination, or bromomethyl ketone (3b) by hydrobromination, of a diazomethyl ketone intermediate. The chloro- and bromomethyl ketones were prepared as described herein by modifications of the methods disclosed by Thompson and Blout, *Biochemistry* 12, 44 (1973), Powers, et al., *Biochem. Biophys. Acta* 485, 156 (1977), and Kettner and Shaw, *Biochemistry* 17, 4778 (1978) for chloromethyl ketones; and the method disclosed by Shaw and Ruscica in *J. Biol. Chem.* 243, 6312 (1968) for N-benzyloxycarbonylphenylalanine bromomethyl ketone. The reaction takes place in three steps, set forth in more detail below: first, a mixed anhydride intermediate is formed (but not isolated); then a diazomethyl ketone intermediate is formed (again, not isolated); and finally, the chloromethyl ketone product (3a) or bromomethyl ketone product (3b) is formed and purified.

(i) A solution of the N-protected amino acid (1), or N-protected peptide (2) in dry aprotic solvent including but not limited to ethyl ether, THF, DME or DMF is blanketed with an "inert" gas such as argon (or alternatively nitrogen) and cooled to a temperature between −40° and 5° C. but preferably −20° to −5° C. This solution is most preferably prepared in dry THF under argon and cooled to about −10° C. A solution so prepared is treated in succession with a tertiary amine such as triethylamine, N-methylmorpholine, N-methylpiperidine or triethylenediamine, preferably triethylamine, and an alkylchloroformate such as isobutylchloroformate, ethyl chloroformate, sec-butylchloroformate, or tert-butylchloroformate, preferably, isobutylchloroformate, to yield, in situ, the mixed anhydride intermediate (not shown).

(ii) The resultant mixture is stirred for about 5 to 60 minutes, preferably 10 to 30 minutes, and most preferably 15 minutes, at the above temperature; then the mixture is treated with about 1.5 to 3 equivalents of a solution of diazomethane, preferably 0.2–0.4 molar in ether, and most preferably 2 equivalents of a 0.3M solution. The resultant reaction mixture is most preferably stirred at −10° C. for an additional 10 minutes, then warmed to room temperature for about 4 hours. The mixture can suitably be stirred for an additional 5 to 60 minutes, preferably between 5 to 20 minutes, then warmed to a temperature of between 10° to 50° C., preferably 20° to 30° C. for 1 to 24 hours, preferably 2 to 6 hours.

(iii) To prepare the chloromethyl ketone the diazomethyl ketone so prepared is treated with a hydrochloric acid/acetic acid mixture in a ratio of 1:1 to 1:3 containing about 10 to about 32% water, but preferentially in a ratio of 1:1 containing about 32% water. Similarly, the bromomethyl ketone is prepared by treating the diazomethyl ketone with a hydrobromic acid/acetic acid mixture in a ratio of 1:1 to 1:3, containing about 0 to about 25% water, but preferably in a ratio of 1:2 containing about 25% water. The chloromethyl ketone (3a) or the bromomethyl ketone (3b) is isolated by extractive workup and purified by chromatography or recrystallization. Detailed procedures for the preparation of a chloromethyl ketone (3a) and a bromomethyl ketone (3b) are give in Preparations 5 and 4, respectively.

Step C-1

Step C-1 (Reaction Scheme I) refers to the alkylation of aromatic alcohols (R'OH) with a chloromethyl (3a) or bromomethyl (3b) ketone to obtain aryloxymethyl ketones IA. This can be accomplished by (a) adopting the method of Ando, et al. *Bull. Chem. Soc. Jpn.* 55, 2504 (1982) such that an aromatic alcohol is alkylated by a chloro- or bromomethyl ketone in a polar aprotic solvent by the action of a fluoride salt which under preferred conditions is supported on an inorganic solid. An alternative method (b) is a modification of the procedures of Stoochnoff, et al. *Tet. Lett.*, 21 (1973) and Allen and Gates, *Org. Synth.*, Coll. Vol. 3, 140 (1955), such that an aromatic alcohol is alkylated by a chloro- or bromomethyl ketone in a polar solvent in the presence of an inorganic base and an iodide salt. However, it is generally preferred that the bromomethyl ketone be used in conjunction with method (b) to obtain the desired aryloxy methyl ketone IA.

Thus, in method (b), a solution of bromomethyl ketone (3b) and an aromatic alcohol in a dry polar solvent, including but not limited to THF, DMF, dioxane or dimethyl sulfoxide (DMSO), is treated with an inorganic base such as potassium carbonate, sodium carbonate, sodium methoxide, sodium ethoxide or sodium hydride, and a catalytic amount of an iodide salt such as potassium iodide, sodium iodide or a tetra-(lower-alkyl)ammonium iodide, and stirred for from 5 minutes to 24 hours but preferably 1 to 8 hours with the exclusion of moisture. This reaction is most preferably performed using dry DMF, potassium carbonate, and tetrabutyl ammonium iodide for four hours under argon. Suitable temperature ranges for the reaction are 0° C. to the solvent reflux temperature, but preferably being room temperature (about 20° C.). The aryloxy methyl ketone product is isolated by extractive workup and purified by recrystallization or chromatography. Detailed procedures are provided in Examples 1-4. The requisite aromatic alcohols (phenols) are generally commercially available, or are prepared by conventional methods.

REACTION SCHEME II

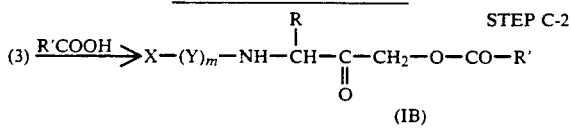

(IB)

REACTION SCHEME II
-continued

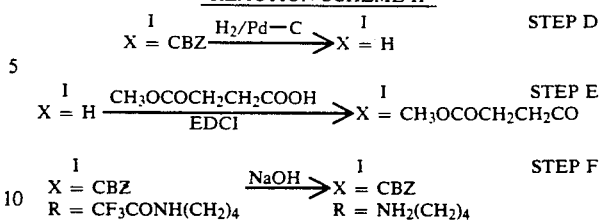

STEP C-2

In Step C-2 (Reaction Scheme II), compounds IB of the invention are obtained by a displacement reaction of an aromatic carboxylic acid (R'COOH) with a peptidyl chloromethyl or bromomethyl ketone (3) of Reaction Scheme I. The procedure is based on methods described by Clark and Miller in *Tetrahedron Lett.*, 599 (1977) and *J. Am. Chem. Soc.*, 99, 498 (1977), and by Clark in *J. Chem. Soc., Chem. Commun.*, 789 (1978). It is generally preferred that the bromomethyl ketone be used rather than the analogous chloromethyl ketone in this reaction. The reaction is conducted in the presence of a fluoride salt, such as a tetra-(lower-alkyl)-ammonium fluoride, KF, LiF, NaF, AgF, or CsF, or any of these fluoride salts bound to silica gel, alumina, diatomaceous earth, and the like. The preferred fluoride salts are potassium fluoride and cesium fluoride, with potassium fluoride being the most preferred. Alternative methods of formation of compounds IB include the reaction of a bromomethyl ketone with an aromatic carboxylic acid in the presence of 1,8-diazobicyclo[5.4.0]undec-7-ene (DBU) (Ono, et al., *Bull. Chem. Soc. Jpn.*, 51, 2401 (1978)), and the reaction of a bromomethyl ketone with the potassium salt of an aromatic carboxylic acid in the presence of a crown ether such as 18-crown-6 (Durst, *Tetrahedron Lett.*, 2421 (1974)); however, the fluoride salt-assisted reaction is the most preferred method. Suitable solvents for the reaction include polar aprotic solvents such as N,N-dimethylformamide (DMF), dimethylsulfoxide (DMSO), dioxane, dimethoxyethane, diglyme, THF, acetonitrile, and acetone. Preferred solvents are DMF and dioxane, with DMF as the most preferred. Suitable temperature ranges for the reaction are 0° C. to the solvent reflux temperature, but preferably the temperature is in the range of 10° C. to 50° C., with the most preferred reaction temperature being room temperature (about 20° C.). The reaction may proceed over a period of from 5 minutes to 2 days. Preferred reaction times are 15 minutes to 6 hours, most preferably 2 hours. Isolation of the product is then generally achieved by extractive workup, optionally followed by purification by recrystallization or chromatography. Detailed procedures are provided in Examples 5 to 9. The requisite aromatic carboxylic acids are generally commercially available, or are prepared by conventional methods; syntheses of specific aromatic carboxylic acids (reaction schemes not shown) are given in Preparations 6 to 12.

Steps D, E and F

Turning again to Reaction Scheme II, N-, O-, or S-protecting groups on compounds of the invention IA or IB as prepared above may then be removed by applying standard methods of deprotection known to those skilled in peptide chemistry, and as described in "The Peptides," Vol. 3; "Protective Groups in Organic Synthesis"; and "Chemistry of the Amino Acids," as cited earlier. By appropriate choice of protecting groups and consideration of deprotection methods, different protecting groups may be removed selectively; for example, a CBZ group may be selectively removed by catalytic hydrogenation in the presence of a Boc group. Additionally, one protecting group may be exchanged with another by an appropriate sequence of deprotection (e.g., Step D) and protection (e.g., Step E) steps, as will be clear to one skilled in the art. An example of the removal of a benzyloxycarbonyl (CBZ) N-protecting group, by hydrogenation over a palladium-on-charcoal catalyst, is shown in Step D of Scheme II; details are given in Example 10.

An example of the addition of a different N-protecting group, in this case the N-methoxysuccinyl group, is shown in Step E of Scheme II; details for this reaction and other examples are given in Examples 11 and 12.

Finally, an example of the selective removal of a side-chain N-protecting group, in this case the N-trifluoroacetyl group on a lysine side chain, is shown in Step F of Scheme II; details for this reaction are given in Example 13.

GENERAL LAST STEP PREPARATIONS

Although the foregoing discussion reflects the best mode of carrying out the invention as currently contemplated by the inventors, other synthetic routes to the compounds of Formula I are conceivable. Thus, methods of preparing compounds of the formula:

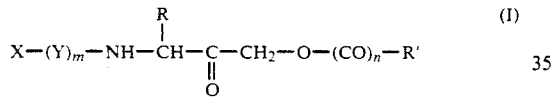

(I)

wherein:
  n is 0 or 1;
  m is 0, 1 or 2;
  x is H or an N-protecting group;
  each Y is independently an optionally protected α-amino acid residue;
  R is an optionally protected α-amino acid side chain that is H or CH$_3$ or that is bonded to the α-carbon atom to which it is attached by a methylene, methine or phenyl radical; and
  R' is optionally substituted aryl; or a pharmaceutically acceptable salt or an optical isomer thereof;
are hereby disclosed, said methods comprising:
  (1) Reacting an optionally substituted aromatic alcohol or aromatic carboxylic acid with an optionally protected peptidyl bromomethylketone, chloromethylketone, iodomethylketone, tosyloxymethylketone, methanesulfonyloxymethylketone, and the like, or an optionally protected α-amino acid bromomethylketone chloromethylketone, iodomethylketone, tosyloxymethylketone, methanesulfonyloxymethylketone, and the like; or
  (2) Removing or adding a protecting group at the amino terminus of the Y α-amino acid when present; and/or to any O, S or N atom of the R α-amino acid side chain; and/or at any O, S or N atom of the R' group; or
  (3) Coupling an N-unsubstituted peptidyl (or amino acid) aryloxymethylketone or an N-unsubstituted peptidyl (or amino acid) acyloxymethylketone to an N-protected amino acid or peptide; or
  (4) Where n=1, acylating a peptidyl or amino acid hydroxymethylketone; or
  (5) Where n=0, substituting a halogenated activated aromatic ring with the peptidyl or amino acid hydroxymethyl ketone; or
  (6) (Where n=1 or 0), reacting an optionally substituted amino acid or peptidyl aryloxy- or acyloxymethyl ketone, where at the position of R there is a halogen atom, with an organometallic radical, where the organic portion of the radical corresponds to R in Formula I; or
  (7) Reacting an optionally protected amino acid or peptidyl diazomethylketone with an aromatic alcohol or carboxylic acid; or
  (8) Adding an optionally protected amino acid or peptidyl amide to an aryloxymethyl—or acyloxymethyl—α-halo optionally substituted lower alkyl or arylalkyl ketone; or
  (9) Removing a ketal, thioketal, or dithioketal of the ketone functionality in Formula I; or
  (10) When Formula I contains a free amino group, adding an acid to make a pharmaceutically acceptable acid addition salt; or
  (11) When Formula I contains a free carboxyl group, adding a base to make a pharmaceutically acceptable base addition salt; or
  (12) Exchanging the anion of the acid addition salt by addition of another acid; or
  (13) Exchanging the cation of the base addition salt by adding another base; or
  (14) Resolving an optical isomer of a racemic mixture of a compound of Formula I; or
  (15) Isomerizing a stereoisomer of a compound of Formula I to produce additional stereoisomers.

PREPARATIONS AND EXAMPLES

PREPARATION 1

N-Benzyloxycarbonyl-L-Phenylalanyl-L-Alanine and Other Compounds of Formula (2)

Dicyclohexylcarbodiimide (50 mmol, 10.3 g) was added to a solution of N-benzyloxycarbonyl-L-phenylalanine (Sigma, 50 mmol, 15.0 g) and N-hydroxysuccinimide (Aldrich, 50 mmol, 5.75 g) in 400 mL of anhydrous THF at 0° C. The mixture was stirred at 0° C. for 2 hours, then at room temperature overnight. The mixture was cooled to 0° C., filtered, and the filtrate was rotary evaporated. The residual oil was dissolved in ethyl acetate, washed with aqueous NaHCO$_3$ (2×) and brine, dried (MgSO$_4$), rotary evaporated and dried at high vacuum to provide 19.1 g (96%) of N-CBZ-L-phenylalanine N-hydroxysuccinimide ester as a white solid, m.p. 134°–136° C. [lit. m.p. 136°–137.5° C.; G. R. Pettit, "Synthetic Peptides," Vol. 3, p. 106, Elsevier/-North-Holland, NY (1975)]. Then, following the method of Itoh [M. Itoh, Chem. Pharm. Bull., 20, 664 (1972)], triethylamine (36 mmol, 5.0 mL) was added to a mixture of L-alanine (18 mmol, 1.60 g) in 200 mL of 1:1 dioxane-water. Solid carbon dioxide pieces were added with stirring until pH 8 was achieved. N-benzyloxycarbonyl-L-phenylalanine N-hydroxysuccinimide ester (18 mmol, 7.13 g) was then added with stirring at room temperature. After 16–20 hours, the mixture was acidified by gradual addition of 1N HCl and then diluted with ethyl acetate. The organic phase was separated, washed with water (2×) and brine, dried (MgSO4), rotovapped, and dried at high vacuum to provide 6.19 g (93%) of N-benzyloxycarbonyl-L-phenylalanyl-L-alanine as a white solid, m.p. 160°–164° C. (lit. m.p. 165° C.; G. R. Pettit, "Synthetic Peptides," Vol. 1, p. 141 (1970)).

In a similar manner, by the method described in Preparation 1, the following compounds of Formula (2) were prepared:
(a) N-Benzyloxycarbonyl-L-phenylalanyl-glycine (m.p. 154°–155° C.) from N-benzyloxycarbonyl-L-phenylalanine and glycine;
(b) N-Benzyloxycarbonyl-L-phenylalanyl-O-benzyl-L-serine (m.p. 154°–155° C.) from N-benzyloxycarbonyl-L-phenylalanine and O-benzyl-L-serine; and
(c) N-Benzyloxycarbonyl-L-phenylalanyl-N$^\epsilon$-trifluoroacetyl-L-lysine (m.p. 143°–147° C.) from N-benzyloxycarbonyl-L-phenylalanine and N$^\epsilon$-trifluoroacetyl-L-lysine (A. T. Moore, et al., *J. Chem. Soc.* (C), 2349–2359 (1966)).

Preparation 2(a)

N-Benzyloxycarbonyl-L-Prolyl-L-Valine And Other Compounds of Formula (2)

L-Valine (30 mmol, 3.52 g) and triethylamine (60 mmol, 8.36 mL) were combined in 275 mL of 1:1 dioxane-water. Solid carbon dioxide pieces were added with stirring to achieve pH 8.5, and then N-CBZ-L-proline 4-nitrophenyl ester (Sigma, 30 mmol, 11.11 g) was added to the solution with stirring at room temperature. After 20 hours, the clear yellow solution was acidified by gradual addition of 1N HCl, concentrated by rotary evaporation at reduced pressure, and diluted with ethyl acetate. The organic phase was separated, washed with water (5×) and brine (2×), dried (MgSO4), and rotovapped to give an oil residue. Crystallization of this residue from hot ethyl acetate-hexane afforded 7.15 g (68%) of N-CBZ-L-prolyl-L-valine as a white solid, m.p. 132°–134° C., lit. m.p. 134°–136° C.; G. R. Pettit, "Synthetic Peptides," Vol. 1, 154 (1970).

In a similar manner, by the method described in Preparation 2(a), the following compounds of Formula (2) were prepared:
(a) N-Benzyloxycarbonyl-L-phenylalanyl-O-benzyl-L-threonine (m.p. 153°–156° C.) from N-benzyloxycarbonyl-L-phenylalanine 4-nitrophenyl ester and O-benzyl-L-threonine (obtained by deprotection of commercially available N-Boc-O-benzyl-L-threonine by treatment with trifluoroacetic acid in dichloromethane);
(b) N-Benzyloxycarbonyl-L-phenylalanyl-S-benzyl-L-cysteine (m.p. 137.5°–139.5° C.) from N-benzyloxycarbonyl-L-phenylalanyl 4-nitrophenyl ester and S-benzyl-L-cysteine;
(c) N-Benzyloxycarbonyl-L-phenylalanyl-O-methyl-L-tyrosine (m.p. 176°–178° C.) from N-benzyloxycarbonyl-L-phenylalanine 4-nitrophenyl ester and O-methyl-L-tyrosine; and
(d) N-benzyloxycarbonyl-L-phenylalanyl-L-phenylalanine (m.p. 148°–151° C.) from N-benzyloxycarbonyl-L-phenylalanine 4-nitrophenyl ester and L-phenylalanine.

Preparation 2(b)

N-Benzyloxycarbonyl-D-phenylalanyl-L-prolyl-L-alanine And Other Compounds of Formula (2)

Triethylamine (9.0 mmol, 1.25 mL) was added to a mixture of L-prolyl-L-alanine (Sigma, 4.5 mmol, 838 mg) in 80 mL of 1:1 dioxane-water. After 15 minutes, pieces of solid carbon dioxide were added to the solution until the pH was reduced to pH 8. N-CBZ-D-Phenylalanine 4-nitrophenyl ester (Sigma, 4.5 mmol, 1.89 g) was then added, and the mixture was stirred at room temperature for four days. The clear yellow solution was acidified by gradual addition of 1N HCl, and diluted with ethyl acetate. The organic phase was then separated, washed with water (3×) and brine (2×), dried (MgSO4), and rotary evaporated to give an oil residue. A solution of this residue in ethyl acetate was fractionally extracted with three solutions of 80 mg NaHCO3 in 10 mL water. These aqueous extracts were combined, acidified, and extracted with ethyl acetate. The resulting ethyl acetate solution was washed with brine, dried (MgSO4), evaporated, and dried at high vacuum to provide 1.45 g (69%) of N-CBZ-D-phenylalanyl-L-valyl-L-alanine as a viscous oil, in sufficient purity for the next step.

In a like manner, by methods described in Preparations 1–2, via the (prepared or commercially available) N-hydroxysuccinimide active ester or (commercially available) 4-nitrophenyl ester, the following compounds of Formula (2) are prepared:
(a) N-acetyl-D,L-phenylalanyl-O-benzyl-L-serine from N-acetyl-D,L-phenylalanine 4-nitrophenyl ester and O-benzyl-L-serine;
(b) N-benzoyl-L-phenylalanyl-L-alanine from N-benzoyl-L-phenylalanine and L-alanine;
(c) N-Boc-L-leucyl-L-methionine from N-Boc-L-leucine 4-nitrophenyl ester and L-methionine; and
(d) N-tosyl-glycyl-L-phenylalanyl-L-alanine from N-tosyl-glycine and L-phenylalanyl-L-alanine.

Preparation 3

N-Benzyloxycarbonyl-L-leucyl-L-phenylalanine And Other Compounds of Formula (2)

To a mixture of N-benzyloxycarbonyl-L-leucine (2.7 g, 10.2 mmol), L-phenylalanine methyl ester hydrochloride (2.2 g, 10.2 mmol), and triethylamine (1.4 mL, 10.2 mmol) in dry THF (150 mL) was added N-ethyl-N'-dimethylaminopropyl-carbodiimide (EDCI) (2.2 g, 11.2 mmol) with stirring at room temperature. After the mixture was stirred overnight at room temperature, it was rotary evaporated. The residue was mixed with ethyl acetate and then washed successively with water, 1N HCl, and brine; the solution was dried (MgSO4) and evaporated to give a white solid residue. Recrystallization (EtOAc-hexane) gave 2.9 g (66%) of N-benzyloxycarbonyl-L-leucyl-L-phenylalanine methyl ester, m.p. 91°–93° C. A mixture of this ester (2.8 g, 6.6 mmol) in 2:1 dioxane-water (150 mL) was treated at 0° C. with 1N NaOH solution (7.3 mmol). After stirring the solution for 2–3 hours at room temperature, it was acidified at 0° C. by the addition of 1N HCl, and then rotary evaporated. The residue was mixed with ethyl acetate and then washed successively with water, 1N HCl, and brine; the solution was dried (MgSO4) and evaporated to give 2.7 g of N-benzyloxycarbonyl-L-leucyl-L-phenylalanine as a white solid, m.p. 120°–122° C.

In a similar manner, the following compound of Formula (2) was prepared:
(a) N-Benzyloxycarbonyl-L-leucyl-L-leucine (m.p. 70°–76° C.) from N-benzyloxycarbonyl-L-leucine and L-leucine methyl ester hydrochloride.

Preparation 4

N-Benzyloxycarbonyl-L-phenylalanyl-L-alanine Bromomethyl Ketone And Other Compounds of Formula (3a)

N-Benzyloxycarbonyl-L-phenylalanyl-L-alanine (5.0 g, 13.4 mmol) was dissolved in dry THF (25 mL), blanketed with argon gas and cooled in an ice/acetone bath (−10° C.). The stirred solution was treated with N-methylmorpholine (1.64 mL, 14.9 mmol) followed by isobutylchloroformate (1.84 mL, 14.2 mmol) over 5 minutes. The resulting suspension was stirred a further 15 minutes at −10° C., treated with diazomethane in ether (100 mL, approx. 0.3M, prepared from "Diazald" (Aldrich) according to the supplier's directions) and warmed to room temperature over 4 hours.

A 1:1 solution of HOAc and 50% HBr (26 mL) was added dropwise to the reaction mixture. After stirring a further 15 minutes, the reaction mixture was transferred to a separatory funnel with the aid of 500 mL of EtOAc. The aqueous layer was discarded; the organic fraction was washed, in succession, with water (1×100 mL), saturated NaCl solution (2×100 mL) and saturated bicarbonate (1×100 mL), dried (anydrous $Na_2SO_4$), and evaporated to dryness. The residue was triturated with ether/hexane (1:2) to yield an off-white solid (5.1 g, 84%), suitable for further manipulation. A recrystallized sample (EtOAc) gave m.p. 138°–139° C.

In a similar manner, by the method described in Preparation 4, the following compounds of Formula (3a) were prepared:

(a) N-benzyloxycarbonyl-L-phenylalanine bromomethyl ketone (m.p. 103°–105° C.) from N-benzyloxycarbonyl-L-phenylalanine;

(b) N-benzyloxycarbonyl-L-phenylalanyl-glycine bromomethyl ketone (m.p. 96.5°–97.5° C.) from N-benzyloxycarbonyl-L-phenylalanyl-glycine;

(c) N-benzyloxycarbonyl-L-phenylalanyl-L-phenylalanine bromomethyl ketone (m.p. 175°–176° C.) from N-benzyloxycarbonyl-L-phenylalanyl-L-phenylalanine;

(d) N-benzyloxycarbonyl-L-phenylalanyl-O-benzyl-L-serine bromomethyl ketone (m.p. 135°–137° C., dec) from N-benzyloxycarbonyl-L-phenylalanyl-O-benzyl-L-serine;

(e) N-benzyloxycarbonyl-L-phenylalanyl-S-benzyl-L-cysteine bromomethyl ketone (m.p. 122.5°–123.5° C., dec) from N-benzyloxycarbonyl-L-phenylalanyl-S-benzyl-L-cysteine;

(f) N-benzyloxycarbonyl-L-phenylalanyl-O-benzyl-L-threonine bromomethyl ketone (m.p. 142.5°–144° C.) from N-benzyloxycarbonyl-L-phenylalanyl-O-benzyl-L-threonine;

(g) N-benzyloxycarbonyl-L-prolyl-L-valine bromomethyl ketone (m.p. 88°–91° C.) from N-benzyloxycarbonyl-L-prolyl-L-valine;

(h) N-benzyloxycarbonyl-D-phenylalanyl-L-prolyl-L-alanine bromomethyl ketone (waxy solid) from N-benzyloxycarbonyl-D-phenylalanyl-L-prolyl-L-alanine;

(i) N-Benzyloxycarbonyl-L-phenylalanyl-N$^\epsilon$-trifluoroacetyl-L-lysine bromomethyl ketone (m.p. 177°–177.5° C.) from N-benzyloxycarbonyl-L-phenylalanyl-N$^\epsilon$-trifluoroacetyl-L-lysine;

(j) N-Benzyloxycarbonyl-L-leucyl-L-leucine bromomethyl ketone (m.p. 93°–99° C.) from N-benzyloxycarbonyl-L-leucyl-L-leucine;

(k) N-Benzyloxycarbonyl-L-leucyl-L-phenylalanine bromomethyl ketone (m.p. 127°–129° C.) from N-benzyloxycarbonyl-L-leucyl-L-phenylalanine; and (l) N-Benzyloxycarbonyl-L-leucine bromomethyl ketone (an oil) from N-benzyloxycarbonyl-L-leucine.

Preparation 5

N-Benzyloxycarbonyl-L-phenylalanyl-L-alanine Chloromethyl Ketone and Other Compounds of Formula (3)

By substituting the 1:1 solution of acetic acid and 50% HBr in Preparation 4 with a 1:1 solution of concentrated hydrochloric acid and glacial acetic acid was obtained N-benzyloxycarbonyl-L-phenylalanyl-L-alanine chloromethyl ketone (m.p. 153°–154° C.).

In a like manner, by methods described in Preparations 4 and 5, the following compounds of Formula (3) are prepared:

(a) N-benzyloxycarbonyl-L-phenylalanyl-O-methyl-L-tyrosine bromomethyl ketone from N-benzyloxycarbonyl-L-phenylalanyl-O-methyl-L-tyrosine;

(b) N-acetyl-D,L-phenylalanyl-O-benzyl-L-serine bromomethyl ketone from N-acetyl-D,L-phenylalanyl-O-benzyl-L-serine;

(c) N-benzoyl-L-phenylalanyl-L-alanine-bromomethyl ketone from N-benzoyl-L-phenylalanyl-L-alanine;

(d) N-Boc-L-leucyl-L-methionine bromomethyl ketone from N-Boc-L-leucyl-L-methionine;

(e) N-tosyl-glycyl-L-phenylalanyl-L-alanine bromomethyl ketone from N-tosyl-glycyl-L-phenylalanyl-L-alanine; and (f) N-benzyloxycarbonyl-L-phenylalanyl-glycine chloromethyl ketone from N-benzyloxycarbonyl-L-phenylalanyl-L-glycine.

Preparation 6

2,3,5,6-Tetramethyl-1,4-benzenedicarboxylic Acid (2,3,5,6-Tetramethyl-terephthalic Acid)

2,3,5,6-Tetramethyl-p-xylene-α,α'-diol (5.0 g, 26 mmol) was suspended in 250 mL of distilled acetone, and cooled to 0° C. To a separate solution of chromium (VI) oxide (14.15 g, 0.14 ml) in 50 mL of water was dropwise added concentrated sulfuric acid (14.5 mL, 0.26 mol) at 0° C. during 45 minutes. This mixture was then added dropwise during 30 minutes to the acetone solution, with stirring at 0° C. The mixture was stirred vigorously at 0° C. for 1 hour, then at room temperature for 18 hours. The reaction mixture was concentrated by rotary evaporation, and 1NHCl was added to attain pH 1. The product was precipitated by cooling, then was filtered, washed with water (3×) and diethyl ether (3×), and dried at high vacuum to afford 4.55 g (80%) of the product (HOOC—$C_6(CH_3)_4$—COOH) as a white solid, m.p. >300° C.

Preparation 7

2,6-Dimethyl-1,4-benzenedicarboxylic Acid (2,6-Dimethyl-terephthalic Acid 2,4,6-Trimethylbenzoic acid (mesitoic acid) (10 g, 61 mmol) was suspended in 150 mL of water, and the mixture cooled to 0° C. Sodium hydroxide pellets (7.31 g, 0.18 mol) were gradually added, followed by addition of potassium permanganate (4×7.2 g, 0.18 mol) at four intervals of 30 minutes. The mixture was stirred at room temperature for 2 hours, then heated on a steam bath for 15–30 minutes. Sulfuric acid (200 mL, 9 mol) was added, then sodium bisulfite was carefully and gradually added at 0° C. The precipitated white solid was filtered and then dissolved in 5N ammonium hydroxide. The solution was washed with diethyl ether, then gradually treated dropwise with concentrated sulfuric acid to precipitate the product. Filtration, followed by washing with hot water (4×) and petroleum ether (3×), recrystallization (methanol-water), and drying at high vacuum gave 10.5 g (89%) of the product as a white solid, m.p. >300° C. (ref. W. A. Noyes, *Amer. Chem. J.,* 20, 789 (1898)).

Preparation 8

4-Methoxycarbonyl-2,6-dimethyl-benzoic Acid 2,6-Dimethyl-1,4-benzenedicarboxylic acid (from Preparation 7) (5.0 g, 26 mmol) was suspended in methanol (40 mL), concentrated sulfuric acid (5 mL) was added, and the mixture was heated at reflux for 2 hours. The solution was cooled, and water was added to precipitate the product. Filtration, followed by washing with water (3×) and petroleum ether (3×), and drying at high vacuum gave 2.05 g of the product as a white powder, m.p. 191°–192° C. (ref. W. A. Noyes, cited above).

Preparation 9

4-Aminocarbonyl-2,6-dimethyl-benzoic Acid

4-Methoxycarbonyl-2,6-dimethyl-benzoic acid (from Preparation 8) (250 mg, 1.2 mmol) was dissolved in methanol (50 mL), and the solution cooled to 0° C. Ammonia gas was bubbled into the solution (at 0° C.) for 20 minutes, and then the mixture was sealed into a stainless steel pressure reaction vessel (Parr bomb) under an atmosphere of ammonia. After heating the mixture at 85° C. for 2 days, it was cooled and evaporated. The residue was mixed with ethyl acetate, washed with 1N HCl (3×), water (2×), and brine (3×), dried ($Na_2SO_4$), and rotary evaporated. The residue was purified by silica-gel column chromatography, eluting with dichloromethane/methanol/acetic acid (79:20:1). The product was isolated and triturated with petroleum ether, filtered and dried at high vacuum to afford 120 mg of the product as a white solid, m.p. 238°–240° C. (ref. W. A. Noyes, cited above).

Preparation 10

4-Phenylsulfonamidocarbonyl-2,6-dimethyl-benzoic Acid 2,6-Dimethyl-1,4-benzenedicarboxylic acid (from Preparation 7) (500 mg, 2.6 mmol) and benzene sulfonamide (486 mg, 3.1 mmol) were combined in dry DMF (25 mL), and EDCI (494 mg, 2.6 mmol) was then added with stirring at 0° C. The mixture was stirred for 2 hours at 0° C. and 2 days at room temperature, then 1N HCl (10 mL) was added, and the mixture was extracted with ethyl acetate. The organic phase was washed with 1N HCl (1×), water (5×), and brine (3×); dried ($Na_2SO_4$); and rotary evaporated to give the crude product (used as such in the next step) as a white solid; NMR (acetone-$d_6$) showed 8.0–7.4 ppm (multiplet with a singlet at 7.7 ppm, 7H) and 2.4 ppm (singlet, 6H).

Preparation 11

4-Methoxycarbonyl-benzoic Acid

4-Hydroxymethyl-benzoic acid (9.25 g, 55.6 mmol) was suspended in 460 mL of distilled acetone, and cooled to 0° C. To a separate solution of chromium (VI) oxide (29.9 g, 0.30 mol) in 100 mL of water was dropwise added concentrated sulfuric acid (27.8 mL, 0.52 mol) at 0° C. during 45 minutes. This mixture was then added dropwise during 75 minutes to the acetone solution, with stirring at 0° C., after which the mixture was stirred at room temperature for 18 hours. The reaction mixture was filtered, and the solid washed with acetone. The filtrate was rotary evaporated, and water was added to precipitate the product. This solid was washed with water and dried at high vacuum to afford 9.4 g (94%) of the product (4—$CH_3OCO-C_6H_4-COOH$) as a white solid, m.p. 222.5°–225° C.

Preparation 12

4-Phenylsulfonamidocarbonyl-benzoic Acid

4-Methoxycarbonyl-benzoic acid (from Preparation 11) (5.0 g, 28 mmol) was dissolved in 100 mL of anhydrous dichloromethane. After the addition of DMAP (3.39 g, 28 mmol) and benzenesulfonamide (4.36 g, 28 mmol), EDCI (5.85 g, 31 mmol) was gradually added to the stirred mixture. After 18 hours at room temperature, rotary evaporation of the mixture gave a residue which was mixed with ethyl acetate and 1N HCl. The organic phase was washed with water (1×) and brine (2×), dried ($Na_2SO_4$), rotary evaporated, and dried at high vacuum to afford 8.7 g (98%) of methyl 4-phenylsulfonamidocarbonyl-benzoate (4—$C_6H_5SO_2-NH-CO-C_6H_4-COOCH_3$) as a white solid. A solution of this material (3.2 g, 10 mmol) in 130 mL of dioxane/water (3:1) was cooled to 0° C. 1N Sodium hydroxide was added dropwise, followed by vigorous stirring at 0° C. for 20 minutes, then at room temperature for 2 hours. The mixture was again cooled to 0° C., and then acidified to pH 2 by gradual addition of 1N HCl. The mixture was rotary evaporated, and the aqueous residue was extracted with ethyl acetate (3×). The combined extracts were washed with brine, dried ($Na_2SO_4$), rotary evaporated, and dried at high vacuum to afford the product (4—$C_6H_5SO_2NHCO-C_6H_4-COOH$), m.p. 267°–270° C.

EXAMPLE 1

N-Benzyloxycarbonyl-L-phenylalanyl-O-benzyl-L-threonine Pentafluorophenoxymethyl Ketone N-benzyloxycarbonyl-L-phenylalanyl-O-benzyl-L-threonine bromomethyl ketone (50 mg, 0.084 mmol) and pentafluorophenol (16 mg, 0.084 mmol) were dissolved in dry DMF (4 mL) and blanketed with argon gas. The solution was treated with potassium carbonate (12 mg, 0.09 mmol), a catalytic amount of tetra-n-butylammonium iodide (2 mg) and stirred at room temperature for 4 hours. Ethyl acetate (100 mL) was added. The organic solution was washed with water (1×25 mL) and saturated NaCl solution (4×25 mL), followed by drying over anhydrous $Na_2SO_4$. The solvent was evaporated and the residue was applied to a silica gel column. The N-benzyloxycarbonyl-L-phenylalanyl-O-benzyl-L-threonine pentafluorophenoxymethyl ketone was eluted with EtOAc/Hexane (1:1) under pressure. Evaporation gave a white solid (0.050 g, 85%), m.p. 140°–141° C.

EXAMPLE 2

N-Benzyloxycarbonyl-L-phenylalanyl-L-alanine Pentafluorophenoxymethyl Ketone N-Benzyloxycarbonyl-L-phenylalanyl-L-alanine bromomethyl ketone (3.7 g) and pentafluorophenol (1.52 g) were dissolved in dry DMF (100 mL) and blanketed with argon. The solution was treated with potassium carbonate (1.14 g) and tetra-n-butylammonium iodide (100 mg) and stirred at room temperature for 4 hours. Ethyl acetate (750 mL) was added. The organic solution was washed with water (1×100 mL) then saturated sodium chloride solution (4×100 mL), dried over anhydrous sodium sulfate and evaporated to a solid residue. The product N-benzyloxycarbonyl-L-phenylalanyl-L-alanine pentafluorophenoxymethyl ketone was recrystallized from EtOAc to yield a white solid (2.69 g, 59%), m.p. 175° C.

In a similar manner, by the methods described in Examples 1 and 2, the following compounds of Formula 1A were prepared:

(a) N-benzyloxycarbonyl-L-phenylalanyl-L-alanine 2,3,5,6-tetrafluorophenoxymethyl ketone (m.p. 171°-172.5° C.) from N-benzyloxycarbonyl-L-phenylalanyl-L-alanine bromomethyl ketone and 2,3,5,6-tetrafluorophenol;

(b) N-benzyloxycarbonyl-L-phenylalanyl-L-alanine 4-ethoxycarbonyl-phenoxymethyl ketone (m.p. 152°-155° C.) from N-benzyloxycarbonyl-L-phenylalanyl-L-alanine bromomethyl ketone and 4-ethoxycarbonyl-phenol (ethyl 4-hydroxybenzoate);

(c) N-benzyloxycarbonyl-L-phenylalanyl-L-alanine 2-methoxycarbonyl-phenoxymethyl ketone (m.p. 150°-152° C.) from N-benzyloxycarbonyl-L-phenylalanyl-L-alanine bromomethyl ketone and 2-methoxycarbonyl-phenol (methyl 2-hydroxybenzoate);

(d) N-benzyloxycarbonyl-L-phenylalanyl-L-alanine 4-acetamido-phenoxymethyl ketone (m.p. 205°-207° C.) from N-benzyloxycarbonyl-L-phenylalanyl-L-alanine bromomethyl ketone and 4-acetamidophenol;

(e) N-benzyloxycarbonyl-L-phenylalanyl-L-alanine 2-acetamido-phenoxymethyl ketone (m.p. 191°-192° C.) from N-benzyloxycarbonyl-L-phenylalanyl-L-alanine bromomethyl ketone and 2-acetamidophenol;

(f) N-benzyloxycarbonyl-L-phenylalanyl-L-alanine 2-carbamoyl-phenoxymethyl ketone (m.p. 166°-168° C.) from N-benzyloxycarbonyl-L-phenylalanyl-L-alanine bromomethyl ketone and 2-carbamoylphenol (2-hydroxy-benzamide);

(g) N-benzyloxycarbonyl-L-phenylalanyl-L-alanine 4-nitrophenoxymethyl ketone (m.p. 159° C., dec) from N-benzyloxycarbonyl-L-phenylalanyl-L-alanine bromomethyl ketone and 4-nitrophenol;

(h) N-benzyloxycarbonyl-L-phenylalanyl-L-alanine 3,5-bis(trifluoromethyl)-phenoxymethyl ketone (m.p. 178°-179.5° C.) from N-benzyloxycarbonyl-L-phenylalanyl-L-alanine bromomethyl ketone and 3,5-bis(trifluoromethyl)phenol;

(i) N-benzyloxycarbonyl-L-phenylalanine 4-nitrophenoxymethyl ketone (m.p. 114°-115° C.) from N-benzyloxycarbonyl-L-phenylalanine bromomethyl ketone and 4-nitrophenol;

(j) N-Benzyloxycarbonyl-L-phenylalanyl-N$^\epsilon$-trifluoroacetyl-L-lysine pentafluorophenoxymethyl ketone (m.p. 197°-198° C.) from N-benzyloxycarbonyl-L-phenylalanyl-N$^\epsilon$-trifluoroacetyl-L-lysine bromomethyl ketone and pentafluorophenol;

(k) N-Benzyloxycarbonyl-L-leucyl-L-leucine pentafluorophenoxymethyl ketone (m.p. 88.5°-89.5° C.) from N-benzyloxycarbonyl-L-leucyl-L-leucine bromomethyl ketone and pentafluorophenol;

(l) N-Benzyloxycarbonyl-L-leucyl-L-phenylalanine pentafluorophenoxymethyl ketone (m.p. 139.5°-140.5° C.) from N-benzyloxycarbonyl-L-leucyl-L-phenylalanine bromomethyl ketone and pentafluorophenol;

(m) N-Benzyloxycarbonyl-L-phenylalanyl-glycine pentafluorophenoxymethyl ketone (m.p. 110°-115° C.) from N-benzyloxycarbonyl-L-phenylalanyl-glycine bromomethyl ketone and pentafluorophenol;

(n) N-Benzyloxycarbonyl-L-phenylalanyl-O-benzyl-L-serine pentafluorophenoxymethyl ketone (m.p. 144°-146.5° C.) from N-benzyloxycarbonyl-L-phenylalanyl-O-benzyl-L-serine bromomethyl ketone and pentafluorophenol;

(o) N-Benzyloxycarbonyl-L-phenylalanyl-L-alanine 2-trifluoromethylphenoxymethyl ketone (m.p. 158°-159° C.) from N-benzyloxycarbonyl-L-phenylalanyl-L-alanine bromomethyl ketone and 2-trifluoromethylphenol;

(p) N-Benzyloxycarbonyl-L-phenylalanyl-L-alanine 2-methyl-6-tert-butyl-phenoxymethyl ketone (m.p. 152.5°-154.5° C.) from N-benzyloxycarbonyl-L-phenylalanyl-L-alanine bromomethyl ketone and 2-methyl-6-tert-butyl-phenol;

(q) N-Benzyloxycarbonyl-L-phenylalanyl-L-alanine 2-methyl-1-naphthyloxymethyl ketone (m.p. 167.5°-169.5° C.) from N-benzyloxycarbonyl-L-phenylalanyl-L-alanine bromomethyl ketone and 2-methyl-1-naphthol;

(r) N-Benzyloxycarbonyl-L-phenylalanyl-L-alanine 2,4-dinitro-phenoxymethyl ketone (m.p. 163°-165° C.) from N-benzyloxycarbonyl-L-phenylalanyl-L-alanine bromomethyl ketone and 2,4-dinitro-phenol;

(s) N-Benzyloxycarbonyl-L-leucine 2-nitrophenoxymethyl ketone (oil; $[\alpha]_D$ —14.6° (acetone)) from N-benzyloxycarbonyl-L-leucine bromomethyl ketone and 2-nitrophenol;

(t) N-Benzyloxycarbonyl-L-leucine 3-nitrophenoxymethyl ketone (oil; $[\alpha]_D$ —9.1° (acetone) from N-benzyloxycarbonyl-L-leucine bromomethyl ketone and 3-nitrophenol; and (u) N-Benzyloxycarbonyl-L-leucine 4-nitrophenoxymethyl ketone (oil; $[\alpha]_D$ —0.3° (acetone)) from N-benzyloxycarbonyl-L-leucine bromomethyl ketone and 4-nitrophenol.

EXAMPLE 3

N-Benzyloxycarbonyl-L-phenylalanyl-L-alanine 2,6-dimethylphenoxymethyl Ketone N-Benzyloxycarbonyl-L-phenylalanyl-L-alanine bromomethyl ketone (50 mg, 0.11 mmol) and 2,6-dimethylphenol (14 mg) were dissolved in dry DMF (5 mL) and blanketed with argon gas. The solution was treated with potassium iodide on alumina (80 mg, KF-alumina, 2:3) and stirred overnight at room temperature. Ethyl acetate was added and the inorganic salts were removed by filtration. The organic filtrate was washed with saturated NaCl solution (4×25 mL), then dried over anhydrous sodium sulfate. The solvent was evaporated and the residue was applied to a silica gel column. Then N-benzyloxycarbonyl-L-phenylalanyl-L-alanine 2,6- dimethylphenoxymethyl ketone was eluted with EtOAc/hexane (1:1) under pressure. Evaporation gave a white solid (30 mg, 49%), m.p. 167°-168° C.

EXAMPLE 4

N-Benzyloxycarbonyl-L-phenylalanyl-L-alanine 4-nitro-phenoxymethyl Ketone

N-Benzyloxycarbonyl-L-phenylalanyl-L-alanine chloromethyl ketone (50 mg, 0.13 mmol) and 4-nitrophenol (22 mg, 0.16 mmol) were dissolved in dry DMF. The solution was treated with potassium carbonate (17 mg, 0.12 mmol), a catalytic amount of tetra-n-butylammonium iodide (2 mg) and blanketed with argon. After stirring for 16 hours, the reaction mixture was diluted with ethyl acetate (100 mL), then washed with water (1×25 mL) and saturated NaCl solution (4×20 mL). The organic layer was dried with anhydrous sodium sulfate, concentrated to a solid and purified by chromatography to yield N-benzyloxycarbonyl-L-phenyl-alanyl-L-alanine 4-nitrophenoxymethyl ketone (20 mg, 35%), identical to the material obtained from the bromomethyl ketone (described in Example 2(g) above).

In a like manner, by methods described in Examples 1-4, the following compounds are prepared:
(a) N-benzyloxycarbonyl-L-phenylalanyl-O-methyl-L-tyrosine pentafluorophenoxymethyl ketone from N-benzyloxycarbonyl-L-phenylalanyl-O-methyl-L-tyrosine bromomethyl ketone and pentafluorophenol;
(b) N-acetyl-D,L-phenylalanyl-O-benzyl-L-serine pentafluorophenoxymethyl ketone from N-Acetyl-D,L-phenylalanyl-O-benzyl-L-serine bromomethyl ketone and pentafluorophenol;
(c) N-benzoyl-L-phenylalanyl-L-alanine pentafluorophenoxymethyl ketone from N-benzoyl-L-phenylalanyl-L-alanine bromomethyl ketone and pentafluorophenol;
(d) N-Boc-L-leucyl-L-methionine pentafluorophenoxymethyl ketone from N-Boc-L-leucyl-L-methionine bromomethyl ketone and pentafluorophenol; and
(e) N-tosyl-glycyl-L-phenylalanyl-L-alanine pentafluorophenoxymethyl ketone from N-tosyl-glycyl-L-phenylalanyl-L-alanine bromomethyl ketone and pentafluorophenol.

EXAMPLE 5

N-Benzyloxycarbonyl-L-phenylalanyl-L-alanine 2,6-bis(trifluoromethyl)benzoyloxymethyl Ketone Anhydrous potassium fluoride (0.39 mmol, 23 mg) was added to a solution of N-CBZ-L-phenylalanyl-L-alanine bromomethyl ketone (0.16 mmol, 73 mg) in 10 mL of anhydrous DMF. The mixture was stirred 3 minutes at room temperature, 2,6-bis(trifluoromethyl)-benzoic acid (Aldrich, 0.16 mmol, 42 mg) was added, and the mixture was stirred 2 hours at room temperature. The mixture was diluted with 100 mL of ethyl ether, washed with water (5×) and brine, dried (MgSO$_4$), rotovapped, and dried at high vacuum to afford 70 mg (68%) of the product as a white solid, m.p. 158°-164° C.; [α]$_D^{20}$ −25.9° (c=0.54, acetone); I.R. (KBr) 1765, 1745, 1695, 1665 cm$^{-1}$.

EXAMPLE 6

N-Benzyloxycarbonyl-L-phenylalanyl-S-benzyl-L-cysteine 2,4,6-trimethylbenzoyloxymethyl Ketone Anhydrous potassium fluoride (0.29 mmol, 17 mg) was added to a solution of N-CBZ-L-phenylalanyl-S-benzyl-L-cysteine bromomethyl ketone (0.12 mmol, 71 mg) in 10 mL of anhydrous DMF. The mixture was stirred for 3 minutes at room temperature, 2,4,6-trimethylbenzoic acid (Aldrich, 0.12 mmol, 20 mg) was added, and the mixture was stirred 4 hours at room temperature. The mixture was diluted with 100 mL of ethyl ether, washed with water (5%) and brine (3×), dried (MgSO$_4$), and rotovapped to give a slightly yellow solid. This material was recrystallized from ethyl ether to provide 37 mg (46%) of the product as a white powder, m.p. 173°-176° C.; [α]$_D^{20}$ −66.8° (c=0.51, acetone); I.R. (KBr) 1730, 1690, 1660 cm$^{-1}$.

EXAMPLE 7

N-Benzyloxycarbonyl-L-phenylalanyl-L-alanine-1-naphthoyloxymethyl Ketone

Anhydrous potassium fluoride (0.67 mmol, 39 mg) was added to a solution of N-CBZ-L-phenylalanyl-L-alanine bromomethyl ketone (0.22 mmol, 100 mg) in 6 mL of anhydrous DMF. After a few minutes, 1-naphthoic acid (Aldrich, 0.22 mmol, 38 mg) was added, and the mixture was stirred 2 hours at room temperature. The mixture was diluted with 100 mL of ethyl ether, washed with water (4×), aqueous NaHCO$_3$ (1×), and brine (3×), dried (MgSO$_4$), rotovapped, and dried at high vacuum to give 127 mg of a white solid. Recrystallization from ethyl acetate-petroleum ether gave the product as a white powder, m.p. 188°-189.5° C.; [α]$_D^{20}$ −29.1° (c=1.02, DMSO); I.R. (KBr) 1740, 1715, 1685, 1640 cm$^{-1}$.

EXAMPLE 8

N-Benzyloxycarbonyl-D-phenylalanyl-L-prolyl-L-alanine 2,4,6-trimethylbenzoyloxymethyl Ketone Anhydrous potassium fluoride (0.29 mmol, 17 mg) was added to a solution of N-CBZ-D-phenylalanyl-L-alanine bromomethyl ketone (0.13 mmol, 70 mg) in 10 mL of anhydrous DMF. The mixture was stirred for 3 minutes at room temperature, 2,4,6-trimethylbenzoic acid (Aldrich, 0.13 mmol, 22 mg) was added, and the mixture was stirred 3 hours at room temperature. The mixture was diluted with 100 mL of ethyl ether, washed with water (4×) and brine (3×), dried (MgSO$_4$), and rotovapped to give a clear oil residue. This material was crystallized from ethyl ether-hexane to provide 30 mg (37%) of the product as a powder, m.p. 65°-80° C., [α]$_D^{20}$ −82.1° (c=0.56, acetone).

EXAMPLE 9

N-Tosyl-L-phenylalanine 2,4,6-trimethylbenzoyloxymethyl Ketone

Anhydrous potassium fluoride (0.64 mmol, 37 mg) was added to a solution of N-tosyl-L-phenylalanine chloromethyl ketone (Sigma, 0.21 mmol, 75 mg) in 10 mL of anhydrous DMF. After a few minutes, 2,4,6-trimethylbenzoic acid (Aldrich, 0.22 mmol, 37 mg) was added, and the mixture was stirred at room temperature overnight. The mixture was diluted with ethyl ether, washed with water (5×), aqueous NaHCO$_3$ (1×) and brine (3×), dried (MgSO$_4$), and rotovapped to give a light brown solid. Recrystallization from ethyl acetate-petroleum ether gave 38 mg (38%) of the product as an off-white powder, m.p. 102°-103° C.

In a similar manner, by the method described in Examples 5 to 9 (with, in certain cases, additional product purification by silica-gel column chromatography using hexane/EtOAc as eluant), the following compounds of Formula IB were prepared:

(a) N-benzyloxycarbonyl-L-phenylalanine 2,4,6-trimethylbenzoyloxymethyl ketone (m.p. 83.5°–84° C.) from N-benzyloxycarbonyl-L-phenylalanine bromomethyl ketone and 2,4,6-trimethylbenzoic acid;

(b) N-benzyloxycarbonyl-L-phenylalanyl-L-alanine 2,4,6-trimethylbenzoyloxymethyl ketone (m.p. 169°–170° C.) from N-benzyloxycarbonyl-L-phenylalanyl-L-alanine bromomethyl ketone and 2,4,6-trimethylbenzoic acid;

(c) N-benzyloxycarbonyl-L-phenylalanyl-L-alanine 2,6-dimethyl-benzoyloxymethyl ketone (m.p. 157°–163° C.) from N-benzyloxycarbonyl-L-phenylalanyl-L-alanine bromomethyl ketone and 2,6-dimethylbenzoic acid;

(d) N-benzyloxycarbonyl-L-phenylalanyl-L-alanine benzoyloxymethyl ketone (m.p. 164°–165° C.) from N-benzyloxycarbonyl-L-phenylalanyl-L-alanine bromomethyl ketone and benzoic acid;

(e) N-benzyloxycarbonyl-L-phenylalanyl-L-alanine 4-nitrobenzoyloxymethyl ketone (m.p. 157°–161° C.) from N-benzyloxycarbonyl-L-phenylalanyl-L-alanine bromomethyl ketone and 4-nitrobenzoic acid;

(f) N-benzyloxycarbonyl-L-phenylalanyl-L-alanine 4-methoxy-benzoyloxymethyl ketone (m.p. 172°–173° C.) from N-benzyloxycarbonyl-L-phenylalanyl-L-alanine bromomethyl ketone and 4-methoxybenzoic acid;

(g) N-benzyloxycarbonyl-L-phenylalanyl-L-alanine 2,6-dimethoxy-benzoyloxymethyl ketone (m.p. 112°–115° C.) from N-benzyloxycarbonyl-L-phenylalanyl-L-alanine bromomethyl ketone and 2,6-dimethoxybenzoic acid;

(h) N-benzyloxycarbonyl-L-phenylalanyl-L-alanine 3,5-bis(trifluoromethyl)-benzoyloxymethyl ketone (m.p. 165°–168.5° C.) from N-benzyloxycarbonyl-L-phenylalanyl-L-alanine bromomethyl ketone and 3,5-bis(trifluoromethyl)-benzoic acid;

(i) N-benzyloxycarbonyl-L-phenylalanyl-L-alanine 2-amino-6-methyl-benzoyloxymethyl ketone (m.p. 146°–147.5° C.) from N-benzyloxycarbonyl-L-phenylalanyl-L-alanine bromomethyl ketone and 2-amino-6-methylbenzoic acid;

(j) N-benzyloxycarbonyl-L-phenylalanyl-L-alanine 2,6-dichlorobenzoyloxymethyl ketone (m.p. 148°–150° C.) from N-benzyloxycarbonyl-L-phenylalanyl-L-alanine bromomethyl ketone and 2,6-dichlorobenzoic acid;

(k) N-benzyloxycarbonyl-L-phenylalanyl-L-alanine 3,5-dihydroxybenzoyloxymethyl ketone (m.p. 207°–209° C.) from N-benzyloxycarbonyl-L-phenylalanyl-L-alanine bromomethyl ketone and 3,5-dihydroxybenzoic acid;

(l) N-benzyloxycarbonyl-L-phenylalanyl-L-alanine pentafluorobenzoyloxymethyl ketone (m.p. 157°–158° C.) from N-benzyloxycarbonyl-L-phenylalanyl-L-alanine bromomethyl ketone and pentafluorobenzoic acid;

(m) N-benzyloxycarbonyl-L-phenylalanyl-L-alanine 2-naphthoyloxymethyl ketone (m.p. 174°–176° C.) from N-benzyloxycarbonyl-L-phenylalanyl-L-alanine bromomethyl ketone and 2-naphthoic acid;

(n) N-benzyloxycarbonyl-L-phenylalanyl-L-alanine 2-methyl-1-naphthoyloxymethyl ketone (m.p. 166°–167° C.) from N-benzyloxycarbonyl-L-phenylalanyl-L-alanine bromomethyl ketone and 2-methyl-1-naphthoic acid; .

(o) N-benzyloxycarbonyl-L-phenylalanyl-L-alanine 2-methoxy-1-naphthoyloxymethyl ketone (m.p. 133°–134° C.) from N-benzyloxycarbonyl-L-phenylalanyl-L-alanine bromomethyl ketone and 2-methoxy-1-naphthoic acid;

(p) N-benzyloxycarbonyl-L-phenylalanyl-L-alanine 2-ethoxy-1-naphthoyloxymethyl ketone (m.p. 141°–143° C.) from N-benzyloxycarbonyl-L-phenylalanyl-L-alanine bromomethyl ketone and 2-ethoxy-1-naphthoic acid;

(q) N-benzyloxycarbonyl-L-phenylalanyl-L-alanine 9-anthracene-carbonyloxymethyl ketone (m.p. 181°–182° C.) from N-benzyloxycarbonyl-L-phenylalanyl-L-alanine bromomethyl ketone and 9-anthracene-carboxylic acid;

(r) N-benzyloxycarbonyl-L-phenylalanyl-glycine 2,4,6-trimethylbenzoyloxymethyl ketone (m.p. 100°–105° C.) from N-benzyloxycarbonyl-L-phenylalanyl-glycine bromomethyl ketone and 2,4,6-trimethylbenzoic acid;

(s) N-benzyloxycarbonyl-L-phenylalanyl-L-phenylalanine 2,4,6-trimethylbenzoyloxymethyl ketone (m.p. 198°–204° C.) from N-benzyloxycarbonyl-L-phenylalanyl-L-phenylalanine bromomethyl ketone and 2,4,6-trimethylbenzoic acid;

(t) N-benzyloxycarbonyl-L-phenylalanyl-O-benzyl-L-serine 2,4,6-trimethylbenzoyloxymethyl ketone (m.p. 137°–142° C.) from N-benzyloxycarbonyl-L-phenylalanyl-O-benzyl-L-serine bromomethyl ketone and 2,4,6-trimethylbenzoic acid;

(u) N-benzyloxycarbonyl-L-phenylalanyl-O-benzyl-L-threonine 2,4,6-trimethylbenzoyloxymethyl ketone (m.p. 97°–104° C.) from N-benzyloxycarbonyl-L-phenylalanyl-O-benzyl-L-threonine bromomethyl ketone and 2,4,6-trimethylbenzoic acid;

(v) N-benzyloxycarbonyl-L-phenylalanyl-S-benzyl-L-cysteine 2,6-bis(trifluoromethyl)benzoyloxymethyl ketone (m.p. 129°–132° C.) from N-benzyloxycarbonyl-L-phenylalanyl-S-benzyl-L-cysteine bromomethyl ketone and 2,6-bis(trifluoromethyl)benzoic acid;

(w) N-benzyloxycarbonyl-L-prolyl-L-valine 2,6-bis(trifluoromethyl)benzoyloxymethyl ketone (viscous oil) from N-benzyloxycarbonyl-L-prolyl-L-valine bromomethyl ketone and 2,6-bis(trifluoromethyl)benzoic acid;

(x) N-Benzyloxycarbonyl-L-phenylalanyl-N$^\epsilon$-trifluoroacetyl-L-lysine 2,4,6-trimethylbenzoyloxymethyl ketone (m.p. 182°–183° C.) from N-benzyloxycarbonyl-L-phenylalanyl-N$^\epsilon$-trifluoroacetyl-L-lysine bromomethyl ketone and 2,4,6-trimethylbenzoic acid;

(y) N-Benzyloxycarbonyl-L-leucyl-L-leucine 2,4,6-trimethylbenzoyloxymethyl ketone (m.p. 115.5°–118° C.) from N-benzyloxycarbonyl-L-leucyl-L-leucine bromomethyl ketone and 2,4,6-trimethylbenzoic acid;

(z) N-Benzyloxycarbonyl-L-leucyl-L-phenylalanine 2,4,6-trimethylbenzoyloxymethyl ketone (m.p. 140°–142° C.) from N-benzyloxycarbonyl-L-leucyl-L-phenylalanine bromomethyl ketone and 2,4,6-trimethylbenzoic acid;

(aa) N-Benzyloxycarbonyl-L-leucyl-L-leucine 2,6-bis(trifluoromethyl)benzoyloxymethyl ketone (m.p. 141°–142° C.) from N-benzyloxycarbonyl-L-leucyl-L-leucine bromomethyl ketone and 2,6-bis(trifluoromethyl)benzoic acid;

(bb) N-Benzyloxycarbonyl-L-leucyl-L-phenylalanine 2,6-bis(trifluoromethyl)benzoyloxymethyl ketone (m.p. 131°–133° C.) from N-benzyloxycarbonyl-L-leucyl-L-phenylalanine bromomethyl ketone and 2,6-bis(trifluoromethyl)benzoic acid;

(cc) N-Benzyloxycarbonyl-L-phenylalanyl-L-alanine 2,6-difluorobenzyloxymethyl ketone (m.p. 164°–165.5° C.) from N-benzyloxycarbonyl-L-phenylalanyl-L-alanine bromomethyl ketone and 2,6-difluorobenzoic acid;

(dd) N-Benzyloxycarbonyl-L-phenylalanyl-L-alanine 3,4-difluorobenzoyloxymethyl ketone (m.p. 163°–164° C.) from N-benzyloxycarbonyl-L-phenylalanyl-L-alanine bromomethyl ketone and 3,4-difluorobenzoic acid;

(ee) N-Benzyloxycarbonyl-L-phenylalanyl-L-alanine 2,4,6-triisopropylbenzoyloxymethyl ketone (m.p. 167°–169° C.) from N-benzyloxycarbonyl-L-phenylalanyl-L-alanine bromomethyl ketone and 2,4,6-triisopropylbenzoic acid;

(ff) N-Benzyloxycarbonyl-L-phenylalanyl-L-alanine 1-hydroxy-2-naphthoyloxymethyl ketone (m.p. 193°–195° C.) from N-benzyloxycarbonyl-L-phenylalanyl-L-alanine bromomethyl ketone and 2-hydroxy-1-naphthoic acid;

(gg) N-Benzyloxycarbonyl-L-phenylalanyl-L-alanine 2,3,5,6-tetramethyl-4-carboxy-benzoyloxymethyl ketone (m.p. 198°–200° C.) from N-benzyloxycarbonyl-L-phenylalanyl-L-alanine bromomethyl ketone and a 3.5-fold excess of 2,3,5,6-tetramethyl-1,4-benzenedicarboxylic acid (from Preparation 6);

(hh) N-Benzyloxycarbonyl-L-phenylalanyl-L-alanine 2,6-dimethyl-4-methoxycarbonyl-benzoyloxymethyl ketone (m.p. 158°–159° C.) from N-benzyloxycarbonyl-L-phenylalanyl-L-alanine bromomethyl ketone and 2,6-dimethyl-4-methoxycarbonyl-benzoic acid (from Preparation 8);

(ii) N-Benzyloxycarbonyl-L-phenylalanyl-L-alanine 2,6-dimethyl-4-phenylsulfonamidocarbonyl-benzoyloxymethyl ketone (m.p. 158°–159° C.) from N-benzyloxycarbonyl-L-phenylalanyl-L-alanine bromomethyl ketone and 2,6-dimethyl-4-phenylsulfonamidocarbonyl-benzoic acid (from Preparation 10);

(jj) N-Benzyloxycarbonyl-L-phenylalanyl-L-alanine 4-phenylsulfonamidocarbonyl-benzoyloxymethyl ketone (m.p. 222°–223° C.) from N-benzyloxycarbonyl-L-phenylalanyl-L-alanine bromomethyl ketone and 4-phenylsulfonamidocarbonyl-benzoic acid (from Preparation 12);

(kk) N-Benzyloxycarbonyl-L-phenylalanyl-L-alanine 2,6-dimethyl-4-aminocarbonyl-benzoyloxymethyl ketone (m.p. 184°–185° C.) from N-benzyloxycarbonyl-L-phenylalanyl-L-alanine bromomethyl ketone and 2,6-dimethyl-4-aminocarbonyl-benzoic acid (from Preparation 9);

(ll) N-Benzyloxycarbonyl-L-phenylalanyl-glycine 2,6-bis(trifluoromethyl)benzoyloxymethyl ketone (m.p. 99°–100° C.) from N-benzyloxycarbonyl-L-phenylalanylglycine bromomethyl ketone and 2,6-bis(trifluoromethyl)benzoic acid;

(mm) N-Benzyloxycarbonyl-L-phenylalanyl-O-benzyl-L-serine 2,6-bis(trifluoromethyl)benzoyloxymethyl ketone (m.p. 141°–144° C.) from N-benzyloxycarbonyl-L-phenylalanyl-O-benzyl-L-serine bromomethyl ketone and 2,6-bis(trifluoromethyl)benzoic acid; and (nn) N-Benzyloxycarbonyl-L-phenylalanyl-O-benzyl-L-threonine 2,6-bis(trifluoromethyl)benzoyloxymethyl ketone (oil) from N-benzyloxycarbonyl-L-phenylalanyl-O-benzyl-L-threonine bromomethyl ketone and 2,6-bis(trifluoromethyl)benzoic acid.

In a like manner are prepared:

(a) N-benzyloxycarbonyl-L-phenylalanyl-O-methyl-L-tyrosine 2,4,6-trimethylbenzoyloxymethyl ketone from N-benzyloxycarbonyl-L-phenylalanyl-O-methyl-L-tyrosine bromomethyl ketone and 2,4,6-trimethylbenzoic acid;

(b) N-acetyl-D,L-phenylalanyl-O-benzyl-L-serine 2,4,6-trimethylbenzoyloxymethyl ketone from N-acetyl-D,L-phenylalanyl-O-benzyl-L-serine bromomethyl ketone and 2,4,6-trimethylbenzoic acid;

(c) N-benzoyl-L-phenylalanyl-L-alanine 2,4,6-trimethylbenzoyloxymethyl ketone from N-benzoyl-L-phenylalanyl-L-alanine bromomethyl ketone and 2,4,6-trimethylbenzoic acid;

(d) N-Boc-L-leucyl-L-methionine 2,4,6-trimethylbenzoyloxymethyl ketone from N-Boc-L-leucyl-L-methionine bromomethyl ketone and 2,4,6-trimethylbenzoic acid; and (e) N-tosyl-glycyl-L-phenylalanyl-L-alanine 2,4,6-trimethylbenzoyloxymethyl ketone from N-tosyl-glycyl-L-phenylalanyl-L-alanine bromomethyl ketone and 2,4,6-trimethylbenzoic acid.

EXAMPLE 10

L-Phenylalanyl-L-alanine 2,4,6-trimethylbenzoyloxymethylketone Hydrochloride

To a mixture of N-CBZ-L-phenylalanyl-L-alanine 2,4,6-trimethylbenzoyloxymethyl ketone (0.38 mmol, 200 mg) in 100 mL of ethanol containing 150 μL (0.75 mmol) of 5N HCl was added 10% palladium on charcoal (20 mg). This mixture was vigorously stirred under an atmosphere of hydrogen gas for 3 hours, the catalyst was removed by filtration through a bed of Celite, and the filtrate was rotary evaporated under reduced pressure. The residue was then precipitated from ethanol-ethyl ether, washed with ethyl ether, and dried at high vacuum to quantitatively afford the product as a powder, m.p. 123°–126° C.

In a similar manner, from the appropriate N-benzyloxycarbonyl-protected compounds of Formula I, are prepared:

(a) L-phenylalanyl-L-alanine 2,6-bis(trifluoromethyl)-benzoyloxymethyl ketone hydrochloride; and (b) L-phenylalanyl-L-alanine pentafluoro-phenoxymethyl ketone hydrochloride.

EXAMPLE 11

N-Methoxysuccinyl-L-phenylalanyl-L-alanine 2,4,6-trimethylbenzoyloxymethyl Ketone L-Phenylalanyl-L-alanine 2,4,6-trimethylbenzoyloxymethyl ketone hydrochloride (Example 10) (500 mg, 1.16 mmol) was dissolved in anhydrous dichloromethane (30 mL) under an argon atmosphere NMM (255 μl, 2.31 mmol) was added, and the mixture was cooled to 0° C. Monomethyl succinate (168 mg, 1.27 mmol) was added, followed by EDCI (244 mg, 1.27 mmol) and DMAP (10 mg, 0.08 mmol). The mixture was stirred at 0° C. for 2 hours, then at room temperature for 18 hours. The reaction mixture was rotary evaporated and the residue partitioned between ethyl acetate and 1N HCl. The organic phase was washed with water (2×), aqueous NaHCO$_3$, and brine (2×), dried (Na$_2$SO$_4$), and rotary evaporated. The residue was recrystallized (EtOAc-pet. ether) and then further purified by silica-gel column chromatography (EtOAc as eluant), to give 203 mg of the product as a white powder, m.p. 185°-186° C.

In a similar manner, the following compounds of Formula 1B were prepared:
(a) N-(4-Methoxycarbonyl-benzoyl)-L-phenylalanyl-L-alanine 2,4,6-trimethylbenzoyloxymethyl ketone (m.p. 213°-214° C.) from L-phenylalanyl-L-alanine 2,4,6-trimethylbenzoyloxymethyl ketone hydrochloride and 4-methoxycarbonyl-benzoic acid; and
(b) N-(4-phenylsulfonamidocarbonyl-benzoyl)-L-phenylalanyl-L-alanine 2,4,6-trimethylbenzoyloxymethyl ketone (m.p. 182°-185° C.) from 1-phenylalanyl-L-alanine 2,4,6-trimethylbenzoyloxymethyl ketone hydrochloride and 4-phenylsulfonamidocarbonyl-benzoic acid.

EXAMPLE 12

N-Hydroxysuccinyl-L-phenylalanyl-L-alanine 2,4,6-trimethylbenzoyloxymethyl Ketone L-Phenylalanyl-L-alanine 2,4,6-trimethylbenzoyloxymethyl ketone hydrochloride (Example 10) (1.0 g, 2.31 mmol) was dissolved in anhydrous DMF (35 mL) under an argon atmosphere. NMM (255 μL, 2.31 mmol) was added, and the mixture was stirred for 5-10 minutes. Succinic anhydride (693 mg, 6.93 mmol) was added, and the mixture was stirred at room temperature for 18 hours. The reaction mixture was diluted with diethyl ether, washed with 1N HCl (2×), water (5×), and brine (3×), dried ($Na_2SO_4$), and rotary evaporated. The residue was recrystallized (EtOAc-pet. ether) to afford 297 mg of the product as a white powder, m.p. 193°-194° C.

EXAMPLE 13

N-Benzyloxycarbonyl-L-phenylalanyl-L-lysine 2,4,6-trimethylbenzoyloxymethyl ketone, hydrogen oxalate or hydrochloride salt (i) To a stirred solution of N-CBZ-L-phenylalanyl-$N^\epsilon$-trifluoroacetyl-L-lysine 2,4,6-trimethylbenzoyloxymethyl ketone (0.33 mmol, 223 mg) in 1,2-dimethoxyethane (15 mL) was added 1N NaOH (8 to 12 molar equivalents) during a 1-3 hour period at room temperature. After an additional hour at room temperature, the mixture was diluted with THF and then washed with brine (4×). The solution was diluted further with ethyl acetate, dried ($Na_2SO_4$), and then anhydrous oxalic acid (1.1 mmol, 100 mg) was added. Rotary evaporation, followed by trituration with hexane and washing with ethyl ether, gave the crude product (as the hydrochloride salt) as a solid. Further purifiction is achieved by chromatography or recrystallization.

(ii) Alternatively, a solution of N-CBZ-L-phenylalanyl-$N^\epsilon$-trifluoroacetyl-L-lysine-2,4,6-trimethylbenzoyloxymethyl ketone (50 mg) in methanol (25 mL), previously saturated with anhydrous hydrogen chloride, was stirred at room temperature overnight. The solution was then rotary evaported, and the residue was washed with ethyl acetate and ether to give the product (as the hydrochloride salt) as a white solid, m.p. 165°-167° C.(dec); IR (KBr) 1725, 1690, 1655 $cm^{-1}$.

In a similar manner, the following compound is prepared:
(a) N-Benzyloxycarbonyl-L-phenylalanyl-L-lysine pentafluorophenoxymethyl ketone, hydrogen oxalate or hydrochloride salt from N-benzyloxycarbonyl-L-phenylalanyl-$N^{68}$-trifluoroacetyl-L-lysine pentafluorophenoxymethyl ketone.

In the following Examples 14 through 21, the active ingredient is the compound N-benzyloxycarbonyl-L-phenylalanyl-L-alanine 2,4,6-trimethylbenzoyloxymethyl ketone. However, other compounds of the invention can be substituted therefor.

EXAMPLE 14

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE 15

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanerbilt Co.) | 1.0 g |
| flavoring | 0.05 ml |
| colorings | 0.5 mg |
| distilled water | q.s. to 100 ml |

EXAMPLE 16

| Ingredients | Quantity per tablet, mgs. |
|---|---|
| Active ingredient | 25 |
| cornstarch | 20 |
| lactose, sray-dried | 153 |
| magnesium stearate | 2 |

The above ingredients are thoroughly mixed and pressed into single scored tablets.

EXAMPLE 17

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 18

| Ingredients | Quantity per tablet, mgs. |
|---|---|
| Active ingredient | 200 |
| cornstarch | 50 |
| lactose | 145 |
| magesium stearate | 5 |

EXAMPLE 19

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 20

| Ingredients | Quantity per tablet, mgs. |
|---|---|
| Active ingredient | 150 |
| lactose | 92 |

The above ingredients are mixed and introduced into a hard-shell gelatin capsule.

EXAMPLE 21

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 22

Assay for the Inhibition of Cathepsin B

Cathepsin B was purified from bovine spleen by the procedure of Bajkowski and Frankfater (*J. Biol. Chem.* 258, 1645-1649 (1983)). The enzyme was stored at −70° C. in 25 mM acetate buffer, pH 5.1, containing 5 mM $HgCl_2$. Inhibition was assayed by monitoring the scission of a fluorogenic substrate in the absence and persence of a compound of Formula I, according to the following procedure.

The assay buffer (0.10M potassium phosphate, 1 mM ethylene diamine tetraacetic acid, 1 mM dithiothreitol, pH 6.0) was prepared and made anaerobic by several cycles of evacuation and exchange with nitrogen or argon. Two mL of this buffer were placed in a fluorimeter cuvette, thermostatted at 25° C. and kept under a nitrogen or argon atmosphere in a Perkin-Elmer 650-40 fluorimeter. Enzyme (0.5 to 5 microliters of a stock solution, sufficient to give approximately 0.1 fluorescence unit (FU) per minute uninhibited rate) was added, and after 1 to 5 minutes of incubation, substrate added (5 to 10 microliters of a 1 mM stock solution in $Me_2SO$) and the increase in fluorescence continuously followed.

Either of two substrates was used: 7-(benzyloxycarbonyl-phenylalanylarginyl)-4-methylcoumarinamide (Peninsula Laboratories, San Carlos, CA) or 7-(benzoyl-valyl-lysyl-lysyl-arginyl)-4-trifluoromethylcourmarinamide (Enzyme Systems Products, Livermore, CA), for which the fluorimeter excitation and emission wavelengths were 370 and 460 nm, or 400 and 505 nm, respectively. After an initial (uninhibited) rate of substrate hydrolysis was established (1 to 3 minutes), the test compound was added (0.5 to 10 microliters of a stock solution in $Me_2SO$). Fluorescence monitoring was continued, typically for an additional 10-40 minutes.

Cathepsin B inhibition in this assay was characterized by two phenomena: (1) an immediate inhibition, manifest as a decrease in the rate of fluorescent product production immediately after inhibitor addition, and (2) time-dependent inhibition, manifest in the approach to apparent complete inactivation. The second order rate constant for this time dependent phase is our principal criterion of potency, which was obtained from the data as follows. For each compound, assays as above were done for between 3 and 8 different inhibitor concentrations. The rate constants of inactivation for each assay ($k_{obs}$) were obtained by non-linear regression of the fluorescence vs. time traces to either of the equations $$(\text{fluorescence}) = Ae^{-(k_{obs}t)} + B + Ct \text{ or}$$

$$(\text{fluorescence}) = Ae^{-(k_{obs}t)} + B.$$

In some cases the $k_{obs}$ increase linearly with the concentration of inhibitor ([I]), and in others the $k_{obs}$ saturate. The desired second order rate constant for inactivation (k/K) was therefore obtained by regression to either $k_{obs} = (k/K)[I]$ or $k_{obs} = k[I]/(K+[I])$, respectively.

We claim:

1. A method of treating a mammal having a disease-state which is alleviated by treatment with a thiol protease inhibitor, comprising administering to a mammal in need thereof a therapeutically effective amount of a compound of formula (I):

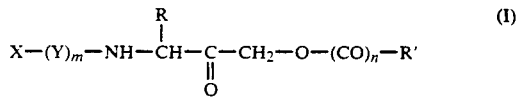

or an optical isomer thereof, or a pharmaceutically acceptable salt thereof, wherein:
n is 0 or 1;
m is 0, 1 or 2;
X is H or an N-protecting group;
each Y is independently an α-amino acid residue having a side chain optionally protected by an O-protecting group, an S-protecting group, or an N-protecting group;
R is hydrogen or a side chain of an α-amino acid wherein said side chain is optionally protected by an O-protecting group, an S-protecting group, or an N-protecting group; and
R' is selected from the group consisting of 2-naphthyl; 9-anthracyl; 2,3,5,6-tetra-methyl-4-carboxyphenyl; 1-naphthyl optionally substituted at the 2-position by lower alkyl, lower alkoxy or trifluoromethyl; and phenyl optionally substituted by 1 to 5 fluoro substituents or by 1 to 3 substituents selected from the group consisting of lower alkyl, lower alkoxy, nitro, halo, acetyl, benzoyl, hydroxy, amino, methylamino, dimethylamino, diethylamino, methylthio, cyano, trifluoromethyl, phenylsulfonamidocarbonyl, —COOH, —CONH$_2$, —COOR$^2$, and —NHCOR$^2$ wherein R$^2$ is lower alkyl.

2. A method of claim 1 wherein X of the compound of formula (I) is selected from the group consisting of hydrogen, acetyl, methoxysuccinyl, hydroxysuccinyl, benzoyl, p-methoxycarbonylbenzoyl (p—CH$_3$OCO—C$_6$H$_4$CO—), p-phenylsulfonamidocarbonylbenzoyl (p—C$_6$H$_5$SO$_2$NHCO—C$_6$H$_4$CO—), Boc, CBZ, or tosyl.

3. A method of claim 1 wherein the compound of formula (I) is selected from the group consisting of:
N-Benzyloxycarbonyl-L-phenylalanyl-L-alanine pentafluorophenoxymethyl ketone;
N-Benzyloxycarbonyl-L-phenylalanyl-O-benzyl-L-threonine pentafluorophenoxymethyl ketone;
N-Benzyloxycarbonyl-L-phenylalanyl-L-alanine 2-carbamoyl-phenoxymethyl ketone;
N-Benzyloxycarbonyl-L-phenylalanyl-L-alanine 4-nitrophenoxymethyl ketone;
N-Benzyloxycarbonyl-L-phenylalanyl-L-alanine 2,6-bis(trifluoromethyl)benzoyloxymethyl ketone;
N-Benzyloxycarbonyl-L-phenylalanyl-L-alanine 2,4,6-trimethylbenzoyloxymethyl ketone;
N-Benzyloxycarbonyl-L-phenylalanyl-O-benzyl-L-serine 2,4,6-trimethylbenzoyloxymethyl ketone;
N-Benzyloxycarbonyl-L-phenylalanyl-S-benzyl-L-cysteine 2,6-bis(trifluoromethyl)benzoyloxymethyl ketone;
N-Benzyloxycarbonyl-L-phenylalanyl-O-benzyl-L-threonine 2,4,6-trimethylbenzoyloxymethyl ketone;
N-Benzyloxycarbonyl-L-phenylalanyl-L-alanine-2-methyl-1-naphthoyloxymethyl ketone;
N-Benzyloxycarbonyl-L-phenylalanyl-glycine 2,4,6-trimethylbenzoyloxymethyl ketone;
N-Methoxysuccinyl-L-phenylalanyl-L-alanine 2,4,6-trimethylbenzoyloxymethyl ketone;
N-Hydroxysuccinyl-L-phenylalanyl-L-alanine 2,4,6-trimethylbenzoyloxymethyl ketone;
N-(4-Phenylsulfonamidocarbonyl-benzoyl)-L-phenylalanyl-L-alanine 2,4,6-trimethylbenzoyloxymethyl ketone;
N-Benzyloxycarbonyl-L-phenylalanyl-L-lysine 2,4,6-trimethylbenzoyloxymethyl ketone, hydrochloride salt; and
N-Benzyloxycarbonyl-L-phenylalanyl-L-alanine 2,3,5,6-tetramethyl-4-carboxy-benzoyloxymethyl ketone.

4. A method of claim 1 wherein the disease-state is selected from the group consisting of tissue damage in myocardial infarction, inflammation, bone resorption, and muscular dystrophy.

5. A method of claim 1 wherein the thiol protease is Cathepsin B.

6. A method of promoting weight gain in a mammal, comprising administering to an animal an effective amount of a compound of formula (I):

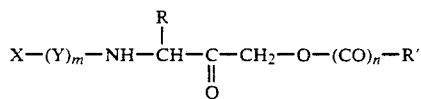

or an optical isomer thereof, or a pharmaceutically acceptable salt thereof, wherein:
n is 0 or 1;
m is 0, 1 or 2;
X is H or an N-protecting group;
each Y is independently an α-amino acid residue having a side chain optionally protected by an O-protecting group, an S-protecting group, or an N-protecting group;
R is hydrogen or a side chain of an α-amino acid wherein said side chain is optionally protected by an O-protecting group, an S-protecting group, or an N-protecting group; and
R' is selected from the group consisting of 2-naphthyl; 9-anthracyl; 2,3,5,6-tetra-methyl-4-carboxyphenyl; 1-naphthyl optionally substituted at the 2-position by lower alkyl, lower alkoxy or trifluoromethyl; and phenyl optionally substituted by 1 to 5 fluoro substituents or by 1 to 3 substituents selected from the group consisting of lower alkyl, lower alkoxy, nitro, halo, acetyl, benzoyl, hydroxy, amino, methylamino, dimethylamino, diethylamino, methylthio, cyano, trifluoromethyl, phenylsulfonamidocarbonyl, —COOH, —CONH$_2$, —COOR$^2$, and —NHCOR$^2$ wherein R$^2$ is lower alkyl.

7. A method for inhibiting thiol protease activity in a mammal, comprising administering to a mammal in need thereof a pharmaceutically effective amount of a compound of formula (I):

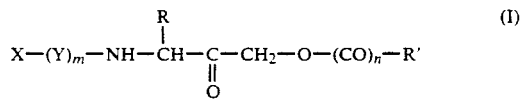

or an optical isomer thereof, or a pharmaceutically acceptable salt thereof, wherein:
n is 0 or 1;
m is 0, 1 or 2;
X is H or an N-protecting group;
each Y is independently an α-amino acid residue having a side chain optionally protected by an O-protecting group, an S-protecting group, or an N-protecting group;
R is hydrogen or a side chain of an α-amino acid wherein said side chain is optionally protected by an O-protecting group, an S-protecting group, or an N-protecting group; and
R' is selected from the group consisting of 2-naphthyl; 9-anthracyl; 2,3,5,6-tetra-methyl-4-carboxyphenyl; 1-naphthyl optionally substituted at the 2-position by lower alkyl, lower alkoxy or trifluoromethyl; and phenyl optionally substituted by 1 to 5 fluoro substituents or by 1 to 3 substituents selected from the group consisting of lower alkyl, lower alkoxy, nitro, halo, acetyl, benzoyl, hydroxy, amino, methylamino, dimethylamino, diethylamino, methylthio, cyano, trifluoromethyl, phenylsulfonamidocarbonyl, —COOH, —CONH$_2$, —COOR$^2$, and —NHCOR$^2$ wherein R$^2$ is lower alkyl.

8. A method of claim 7 wherein the thiol protease is Cathepsin B.

9. A method of claim 8 wherein X of the compound of formula (I) is selected from the group consisting of hydrogen, acetyl, methoxysuccinyl, hydroxysuccinyl, benzoyl, p-methoxycarbonylbenzoyl (p—CH₃OCO—C₆H₄CO—), p-phenylsulfonamidocarbonylbenzoyl (p—C₆H₅SO₂NHCO—C₆H₄CO—), Boc, CBZ, or tosyl.

10. A method of claim 9 wherein the compound of formula (I) is selected from the group consisting of:

N-benzyloxycarbonyl-L-phenylalanyl-L-alanine pentafluorophenoxymethyl ketone;

N-benzyloxycarbonyl-L-phenylalanyl-O-benzyl-L-threonine pentafluorophenoxymethyl ketone;

N-benzyloxycarbonyl-L-phenylalanyl-L-alanine 2-carbamoylphenoxymethyl ketone;

N-benzyloxycarbonyl-L-phenylalanyl-L-alanine 4-nitrophenoxymethyl ketone;

N-benzyloxycarbonyl-L-phenylalanyl-L-alanine 2,6-bis(trifluoromethyl)benzoyloxymethyl ketone;

N-benzyloxycarbonyl-L-phenylalanyl-L-alanine 2,4,6-trimethylbenzoyloxymethylketone;

N-benzyloxycarbonyl-L-phenylalanyl-O-benzyl-L-serine 2,4,6-trimethylbenzoyloxymethyl ketone;

N-benzyloxycarbonyl-L-phenylalanyl-S-benzyl-L-cysteine 2,6-bis(trifluoromethyl)benzoyloxymethyl ketone;

N-benzyloxycarbonyl-L-phenylalanyl-O-benzyl-L-threonine 2,4,6-trimethylbenzoyloxymethyl ketone;

N-benzyloxycarbonyl-L-phenylalanyl-L-alanine-2-methyl-1-naphthoyloxymethyl ketone;

N-benzyloxycarbonyl-L-phenylalanyl-glycine 2,4,6-trimethylbenzoyloxymethyl ketone;

N-methoxysuccinyl-L-phenylalanyl-L-alanine 2,4,6-trimethylbenzoyloxymethyl ketone;

N-hydroxysuccinyl-L-phenylalanyl-L-alanine 2,4,6-trimethylbenzoyloxymethyl ketone;

N-(4-phenylsulfonamidocarbonyl-benzoyl)-L-phenyl-alanyl-L-alanine 2,4,6-trimethylbenzoyloxymethyl ketone;

N-benzyloxycarbonyl-L-phenylalanyl-L-lysine 2,4,6-trimethylbenzoyloxymethyl ketone, hydrochloride salt; and N-benzyloxycarbonyl-L-phenylalanyl-L-alanine 2,3,5,6-tetramethyl-4-carboxy-benzoyloxymethyl ketone.

11. A method of claim 10 wherein the compound of formula (I) is selected from the group consisting of:

N-benzyloxycarbonyl-L-phenylalanyl-L-alanine 2,6-bis(trifluoromethyl)benzoyloxymethyl ketone;

N-benzyloxycarbonyl-L-phenylalanyl-L-alanine 2,4,6-trimethylbenzoyloxymethylketone;

N-benzyloxycarbonyl-L-phenylalanyl-O-benzyl-L-serine 2,4,6-trimethylbenzoyloxymethyl ketone;

N-benzyloxycarbonyl-L-phenylalanyl-S-benzyl-L-cysteine 2,6-bis(trifluoromethyl)benzoyloxymethyl ketone;

N-benzyloxycarbonyl-L-phenylalanyl-O-benzyl-L-threonine 2,4,6-trimethylbenzoyloxymethyl ketone;

N-benzyloxycarbonyl-L-phenylalanyl-L-alanine-2-methyl-1-naphthoyloxymethyl ketone;

N-benzyloxycarbonyl-L-phenylalanyl-glycine 2,4,6-trimethylbenzoyloxymethyl ketone;

N-methoxysuccinyl-L-phenylalanyl-L-alanine 2,4,6-trimethylbenzoyloxymethyl ketone;

N-hydroxysuccinyl-L-phenylalanyl-L-alanine 2,4,6-trimethylbenzoyloxymethyl ketone;

N-(4-phenylsulfonamidocarbonyl-benzoyl)-L-phenyl-alanyl-L-alanine 2,4,6-trimethylbenzoyloxymethyl ketone;

N-benzyloxycarbonyl-L-phenylalanyl-L-lysine 2,4,6-trimethylbenzoyloxymethyl ketone, hydrochloride salt; and N-benzyloxycarbonyl-L-phenylalanyl-L-alanine 2,3,5,6-tetramethyl-4-carboxy-benzoyloxymethyl ketone.

* * * * *